United States Patent

Brain et al.

[11] Patent Number: 4,921,839
[45] Date of Patent: May 1, 1990

[54] ERYTHROMYCIN A 11,12-CARBONATE 9-OXIME DERIVATIVES

[75] Inventors: Edward G. Brain; Eric Hunt; Andrew K. Forrest, all of Betchworth, England

[73] Assignee: Beecham Group p.l.c., England

[21] Appl. No.: 158,543

[22] Filed: Feb. 22, 1988

[30] Foreign Application Priority Data

Feb. 24, 1987 [GB] United Kingdom ............ 8704212
Mar. 11, 1987 [GB] United Kingdom ............ 8705794
Aug. 25, 1987 [GB] United Kingdom ............ 8719990

[51] Int. Cl.$^5$ .................. A61K 31/70; C07H 17/08
[52] U.S. Cl. ................................ 514/29; 536/7.4
[58] Field of Search ............... 536/7.2, 7.4; 514/29

[56] References Cited

U.S. PATENT DOCUMENTS 3,869,444  3/1975  Freiberg ..................... 536/7.4
4,283,527  8/1981  Sciavolino ................... 536/7.4
4,742,049  5/1988  Baker et al. ................. 514/29

Primary Examiner—Johnnie R. Brown
Assistant Examiner—Elli Peselev
Attorney, Agent, or Firm—Jacobs & Jacobs

[57] ABSTRACT

Antibacterially active 11,12-carbonate derivatives of erythromycin 9-(optionally substituted)oxime and 9-imino compounds and their pharmaceutically acceptable ester or acid addition salt thereof:

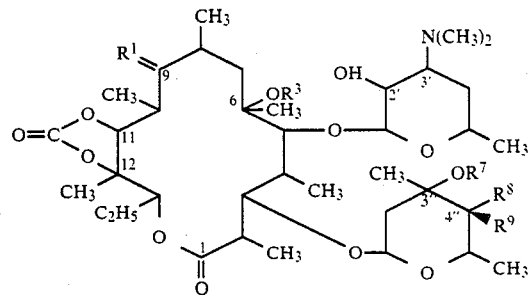

wherein
$R^1$ denotes an oxime group, a substituted oxime group, or an imino group;
$R^3$ denotes a hydrogen atom or an unsubstituted or substituted alkyl group;
$R^7$ denotes hydrogen or methyl;
one of $R^8$ and $R^9$ denotes hydrogen, hydroxy, alkoxy, alkanoyloxy, amino, substituted amino, or a group of the formula $R^4$—$SO_2$—O—, in which $R^4$ denotes an organic group, and the other of $R^8$ and $R^9$ denotes hydrogen, or
$R^8$ and $R^9$ together denote an oxo group, an oxime group, or a substituted oxime group.

6 Claims, No Drawings

ERYTHROMYCIN A 11,12-CARBONATE 9-OXIME DERIVATIVES

The present invention relates to novel chemical compounds, their preparation and their use, and in particular to a novel class of erythromycin derivatives. These compounds have antibacterial properties, in particular against Gram-positive bacteria but also against some Gram-negative bacteria, and they are therefore of use in the treatment of bacterial infections in humans and animals caused by a wide range of organisms. Erythromycin was first described in U.S. Pat. No. 2,653,899 (R.L. Bunch et al; Eli Lilly). The structure of erythromycins can be represented as follows:

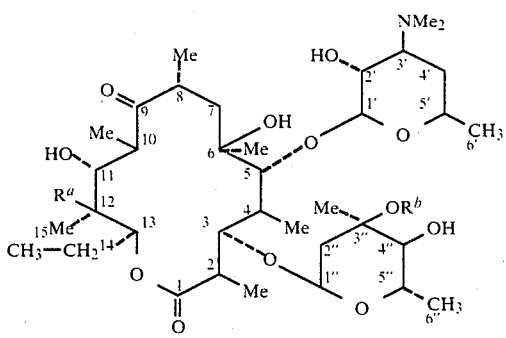

in which
$R^a$ denotes hydrogen or hydroxy and
$R^b$ denotes hydrogen or methyl.

The basic erythromycin structure comprises:
(i) a 14-membered lactone ring, referred to as the erythronolide ring, numbered with unprimed digits as shown in the above formula,
(ii) a first sugar ring, known as the desosamine ring, numbered with single-primed digits, and
(iii) a second sugar ring, known as the cladinose ring, numbered with double-primed digits.

The erythronolide ring can exist in two forms:
erythronolide A (in which $R^a$ = OH)
erythronolide B (in which $R^a$ = H).

The four main naturally occurring erythromycins are as follows:

| Erythromycin | $R^a$ | $R^b$ |
| --- | --- | --- |
| A | OH | $CH_3$ |
| B | H | $CH_3$ |
| C | OH | H |
| D | H | H | of which erythromycin A is by far the most important.

Erythromycins, and in particular erythromycin A, are antibiotics widely employed clinically in the treatment of infections caused by Gram-positive and some Gram-negative bacteria. A major drawback of erythromycins is their poor acid stability, resulting in poor and erratic oral absorption.

Numerous attempts have been made to modify erythromycin to produce derivatives having improved acid stability without loss of the antibacterial activity.

Among the many erythromycin derivatives that have been described in the literature are the 11,12-carbonates of erythromycin A (W. Slawinski et al, *Recueil, J. Royal Netherlands Chem. Soc.* 94 236 (1975)); of 9-dihydroerythromycin A (T. Glabski et al. *Roczniki Chemii* 50 1281 (1976)); of erythromycylamine (I. Dziegielewska et al. *Polish J. Chem.* 53 2551 (1979)); of 8-hydroxyerythromycin A (K. Krowicki, *J. Antibiotics* XXVII (8) 626 (1974)); of erythromycin A L-aspartate salt (H. Bojarska-Dahlig et al, *J. Antibiotics* XXIX (9) 907 (1976)); of various 4"-modified erythromycin A derivatives (U.S. Pat. No. 4,150,220, F.C. Scavolino, Pfizer); of erythromycylamine and various 2'-derivatives thereof (U.S. Pat. No. 4,283,527, F.C. Sciavolino, Pfizer); and of certain erythromycin A 6,9-hemiacetal derivatives (EP 0 081 305, Taisho; JP 58.090 595, Taisho).

All of the above 11,12-carbonate derivatives are prepared by the reaction of an appropriate erythromycin compound with ethylene carbonate in the presence of a base, and a modified method of carrying out that process has recently been described (EP 0 119 431, Polfa).

In addition, the conversion of erythromycin A 11,12-carbonate to 6-O-acyl derivatives thereof (JP-62-142-194-A, Toyo Jozo KK) and the conversion of the 2'-acetyl derivative of erythromycin A 11,12-carbonate and of the 6,9-hemiketal derivatives thereof to corresponding 4"-deoxy derivatives (U.S. Pat. No. 4,681.872 and 4,686,207, both to Frieborq et al, Abbott Laboratories) have also been recently described.

Despite the many references to 11,12-carbonates of erythromycin and its derivatives, there has been no disclosure of 11,12-carbonates of erythromycin 9-oxime and 9-oxime ethers. Our attempts to prepare erythromycin A 9-oxime 11,12-carbonate both by reaction of ethylene carbonate with erythromycin 9-oxime analogously to the above method and by conversion of the 9-keto group of erythromycin A 11,12-carbonate have met with failure.

We have now found that it is possible to prepare 11,12-carbonate derivatives of erythromycin 9-oxime and 9-oxime ethers by another method.

The present invention provides antibacterially active 11,12-carbonate derivatives of erythromycin 9-(optionally substituted)oxime and 9-imino compounds.

In particular, the present invention provides a compound of the general formula I or a pharmaceutically acceptable ester or acid addition salt thereof:

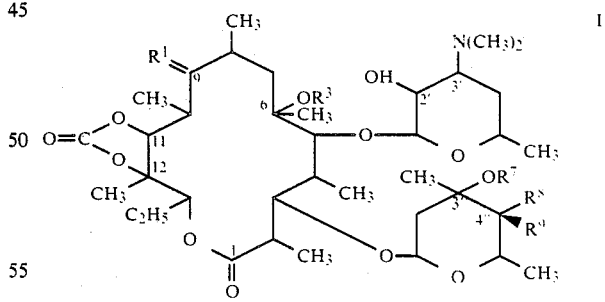

wherein
$R^1$ denotes an oxime group, a substituted oxime group, or an imino group;
$R^3$ denotes a hydrogen atom or an unsubstituted or substituted alkyl group;
$R^7$ denotes hydrogen or methyl;
one of $R^8$ and $R^9$ denotes hydrogen, hydroxy, alkoxy, alkanoyloxy, amino, substituted amino, or a group of the formula $R^d$—$SO_2$—$O$—, in which $R^d$ denotes an organic group, and the other of $R^8$ and $R^9$ denotes hydrogen, or $R^8$ and $R^9$ together denote an oxo group, an oxime group, or a substituted oxime group.

The term 'hydrocarbon' as used herein includes groups having up to 18 carbon atoms, suitably up to 10 carbon atoms, conveniently up to 6 carbon atoms. Suitable hydrocarbon groups include $(C_{1-6})$alkyl, $(C_{2-6})$alkenyl, $(C_{2-6})$alkynyl, $(C_{3-7})$cycloalkyl, aryl, $(C_{3-7})$cycloalkyl$(C_{1-6})$alkyl, aryl$(C_{1-6})$alkyl, $(C_{1-6})$alkyl$(C_{3-7})$cycloalkyl, and $(C_{1-6})$alkylaryl.

Examples of suitable optional substituents for the above-mentioned hydrocarbon groups include, heterocyclyl, substituted heterocyclyl, amino, (mono, di, or tri)-$(C_{1-6})$-alkylamino, $(C_{1-6})$alkanoylamino, hydroxy, $(C_{1-6})$alkoxy, $(C_{1-6})$alkoxy$(C_{1-6})$alkoxy, alkenyloxy, alkynyloxy, aryloxy, aralkyloxy, mercapto, $(C_{1-6})$alkylthio, alkenylthio, alkynylthio, arylthio, aralkylthio, heterocyclythio, sulphamoyl, carbamoyl, substituted carbamoyl, amidino, guanidino, nitro, oxo, formyl, chloro, bromo, fluoro, cyano, thiocyanato, carboxy, carboxy salts, carboxy esters, $(C_{1-6})$alkanoyloxy, acyl, arylcarbonyl, arylcarbonyloxy, heterocyclylcarbonyl and heterocyclylcarbonyloxy.

Any alkyl group or moiety referred to herein may be straight or branched, unsubstituted or substituted, and may contain, for example, up to 12 carbon atoms, suitably up to 6 carbon atoms. In particular, the alkyl group or moiety may be an unsubstituted or substituted methyl, ethyl, n-propyl, iso-propyl, n-butyl, sec-butyl, isobutyl or tert-butyl group. Examples of suitable optional substitutents for any such alkyl group or moiety include the above-listed substitutents for hydrocarbon groups, and also the above-listed non-alkyl hydrocarbon groups, for example $(C_{2-6})$alkenyl and aryl groups.

The term 'aryl' as used herein includes phenyl and naphthyl, which may be unsubstituted or substituted by up to five, preferably up to three, groups selected from the above-listed substituents for hydrocarbon groups, and the above-listed hydrocarbon groups, including, for example, substituents selected from halogen, $(C_{1-6})$alkyl, phenyl, $(C_{-6})$alkoxy, halo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkanoyloxy, and $(C_{1-6})$alkanoyl groups.

The term 'acyl' as used herein includes formyl, unsubstituted and substituted hydrocarbon-carbonyl and hydrocarbonoxy-carbonyl groups, including, for example, unsubstituted and substituted alkanoyl, cycloalkylcarbonyl, arylcarbonyl, alkoxycarbonyl, aryloxycarbonyl, and heterocyclylcarbonyl groups. The term 'acyloxy' is used analogously.

The term 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected form halogen, $(C_{1-6})$alkyl, $(C_{1-6})$alkoxy, halo$(C_{1-6})$alkyl, hydroxy, amino, carboxy, carboxy salts, carboxy esters, $(C_{1-6})$alkoxycarbonyl, $(C_{1-6})$alkoxycarbonyl$(C_{1-6})$alkyl, aryl, and oxo groups. Each heterocyclic ring suitably has from 4 to 7, preferably 5 or 6, ring atoms. A fused heterocyclic ring system may include carbocyclic rings and need include only one heterocyclic ring.

The term 'heteroaryl' as used herein means an aromatic heterocyclic ring or ring system, suitably having 5 or 6 ring atoms in each ring.

In one group of compounds of the general formula I, $R^1$ denotes an oxime group (also referred to as a hydroxyimino group, =NOH) or a substituted oxime group (for example, an oxime ether group or an acyl-oxime group). Such compounds may be referred to as erythromycin oxime derivatives. In a second group of compounds of the general formula I, $R^1$ denotes an imino group, and such compounds may be referred to as erythromycin imines.

In the case of the erythromycin oxime and substituted-oxime derivatives according to the invention, $R^1$ may denote a group of the formula II:

$$=O-R^B \qquad \text{II}$$

in which $R^B$ denotes hydrogen or an unsubstituted or substituted hydrocarbon group or an acyl group. Examples of suitable groups denoted by $R^B$ include unsubstituted and substituted alkyl, cycloalkyl, alkenyl, alkynyl, aryl (preferably phenyl) and aralkyl (preferably benzyl) groups, and also unsubstituted and substituted hydrocarbon-carbonyl and hydrocarbonoxy-carbonyl groups, for example unsubstituted and substituted alkanoyl, cycloalkylcarbonyl, arylcarbonyl, alkoxycarbonyl, aralkyloxy carbonyl and aryloxycarbonyl groups; each of the said alkyl groups and moieties suitably having up to 6 carbon atoms.

Examples of suitable substituents for the hydrocarbon group $R^B$ include heterocyclyl, substituted heterocyclyl, amino, $(C_{1-6})$alkanoylamino, (mono, di, or tri)-$(C_{1-6})$-alkylamino, hydroxy, $(C_{1-6})$alkoxy, $(C_{1-6})$alkoxy$(C_{1-6})$alkoxy, alkenyloxy, alkynyloxy, aryloxy, aralkyloxy, mercapto, $(C_{1-6})$alkylthio, alkenylthio, alkynylthio, arylthio, aralkylthio, heterocyclylthio, sulphamoyl, carbamoyl, substituted carbamoyl, amidino, guanidino, nitro, oxo, formyl, chloro, bromo, fluoro, cyano, thiocyanato, carboxy, carboxy salts, carboxy esters, $(C_{1-6})$alkanoyloxy, acyl, arylcarbonyl, arylcarbonyloxy, heterocyclylcarbonyl and heterocyclylcarbonyloxy groups, and also a group of the formula III:

$$-S(O)_n R^C$$

in which n denotes 0, 1 or 2, and $R^C$ denotes a $(C_{1-6})$alkyl, heterocyclyl, or aryl group.

Examples of acyl groups $R^B$ include acetyl and benzyloxycarbonyl groups. Examples of unsubstituted alkyl groups $R^B$ include methyl, ethyl, n-propyl, isopropyl, n-butyl, sec-butyl and tert-butyl groups. An example of an unsubstituted cycloalkyl group $R^B$ is cyclopentyl. Examples of substituted alkyl groups $R^B$ include aralkyl (especially benzyl), heterocyclylalkyl, alkoxyalkyl, alkenyloxyalkyl, alkynyloxyalkyl, aryloxyalkyl, arylalkoxyalkyl, alkoxyalkoxyalkyl (for example, 2-methoxyethoxymethyl), alkylthioalkyl, alkenylthioalkyl, alkynylthioalkyl, arylthioalkyl, aralkylthioalkyl, haloalkyl, hydroxyalkyl, formylalkyl, carboxyalkyl and salts and esters thereof, thiocyanatoalkyl, cyanoalkyl, acylalkyl, carbamoylalkyl, and aminoalkyl groups; each of the said alkyl, alkenyl and alkynyl moieties suitably having up to 6 carbon atoms; each of the said thio derivatives optionally being oxidised to the corresponding sulphoxide or sulphone derivative; and the said amino moiety of the said aminoalkyl groups suitably being of the formula IV:

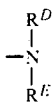

in which each of $R^D$ and $R^E$, which may be identical or different, denotes hydrogen or an unsubstituted or substituted hydrocarbon group, advantageously an alkyl group, preferably having from 1 to 6 carbon atoms, or $R^D$ and $R^E$ and the nitrogen atom to which they are attached together denote an unsubstituted or substituted, unsaturated or saturated heterocyclic ring, optionally containing one or more heteroatoms additional to the said nitrogen atom, each of $R^D$ and $R^E$ preferably denoting a hydrogen atom.

Erythromycin oximes and substituted-oximes having 9-substituents of the type described above have been described in, for example, GB 1 100 504, Pliva Pharmaceuticals; E.H. Massey et al, *Tetrahedron Letters* 1970 No.2 157; G.H. Timms et al, ibid 1971 No.2 195; U.S. Pat. No. 3,681,326, A.M. Von Esch, Abbott Laboratories; U.S. Pat. No. 3,869,445 and U.S. Pat. No. 4,063,014, R. Hallas et al, Abbott Laboratories; and U.S. Pat. No. 4,349,545, S. Gouin d'Ambrieres, Roussel-Uclaf. The erythromycin oxime and substituted oxime derivatives according to the invention can exist in two geometric isomeric forms about the C=N double bond at the 9-position, as indicated by the wavy line in formula II above, namely the E-form and the Z-form. The E-form is generally preferred.

In the case of the erythromycin imine derivatives according to the invention, $R^1$ denotes a group of the formula V:

Erythromycin imine has been described, for example, in G.H. Timms et al, op. cit..

The erythromycin oxime or imine derivatives according to the invention are characterised by a 11,12-carbonate group, —O—CO—O—.

The 6-position of the erythronolide ring in the compounds according to the invention may carry a hydroxy group ($R^3$ denotes hydrogen) or an alkoxy group ($R^3$ denotes unsubstituted or substituted alkyl).

In the latter case, $R^3$ advantageously denotes an unsubstituted or substituted primary alkyl group (i.e. an alkyl group in which the α-carbon atom carries at least two hydrogen atoms). Suitably, the alkyl group may be a lower alkyl group, preferably a $(C_{1-6})$alkyl group, for example a methyl or ethyl group. Examples of substituted alkyl groups denoted by $R^3$ include aralkyl groups, for example a benzyl group, and alkenylalkyl groups, for example an allyl group. Suitably $R^3$ denotes a hydrogen atom or an unsubstituted alkyl group (preferably a lower alkyl group), and especially a hydrogen atom or a methyl group.

Various 6-O-methyl derivatives of erythromycin have been described in EP 0 041 355 A1, EP 0 080 818 A1, EP 0 080 819 A1, and EP 0 158 467 A2 (all Taisho Pharmaceutical).

6-ether derivatives of erythromycin 9-oxime, 9-oxime-ethers and 9-imine have been described in EP 0 194 833 A2 (Beecham).

The —$OR^7$ group in the 3"-position of the cladinose ring may be a hydroxy group or a methoxy group.

Preferably, $R^7$ denotes a methyl group as in erythromycin A.

The 4"-position of the cladinose ring may suitably carry a hydroxy group as in erythromycin A ($R^8$ = H; $R^9$ = OH). Various modifications of the 4"-position of the cladinose ring have previously been described and those modifications may be incorporated in the compounds according to the present invention:

(i) 4"-deoxy-4"-oxo derivatives ($R^8$ + $R^9$ = O =) are described in U.S. Pat. No. 3,842,069 and U.S. Pat. No. 3,884,903, both P.H. Jones et al, Abbott Laboratories, and U.S. Pat. No. 4,150,220, F.C. Sciavolino, Pfizer;

(ii) 4"-epi-hydroxy derivatives ($R^8$ = OH; $R^9$ = H) and 4"-deoxy-4"-alkanoyloxy-4"-epi derivatives ($R^8$ = alkanoyloxy, especially $CH_3COO$—; $R^9$ = H) are described in U.S. Pat. No. 3,884,903, op cit., and U.S. Pat. No. 4,382,085, F.C. Sciavolino, Pfizer;

(iii) 4"-O-alkyl derivatives ($R^8$ or $R^9$ = alkoxy, especially methoxy; the other of $R^8$ and $R^9$ = H) are described in EP 0 080 818 A1, op. cit.;

(iv) 4"-deoxy-4"-amino derivatives ($R^8$ or $R^9$ = amino or substituted amino; the other of $R^8$ and $R^9$ = H) are described in U.S. Pat. No. 4,150,220, op. cit.;

(v) 4"-deoxy-4"-oxime derivatives ($R^8$ + $R^9$ = oxime (=N—OH) or substituted oxime, especially acetyloxime (=N—O—CO—$CH_3$)) are also described in U.S. Pat. No. 4,150,220, op cit.;

(vi) 4"-O-sulphonyl derivatives ($R^8$ = H, $R^9$ = $R^A$—$SO_2$—O—) are described in U.S. Pat. No. 3,836,519, U.S. Pat. No. 3,869,445 and U.S. Pat. No. 4,063,014, all R. Hallas et al, Abbott Laboratories;

(vii) 4"-deoxy derivatives ($R^8$ = $R^9$ = H) are described in JP 58-049396, Toyo Jozo KK.

In the 4"-deoxy-4"-(substituted amino) derivatives, the substituted amino group $R^8$ or $R^9$ may suitably be a group of the formula VI or VII:

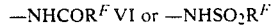

in which $R^F$ denotes a hydrocarbon group.

In the 4"-O-sulphonyl derivatives, in which $R^8$ or $R^9$ denotes a sulphonyloxy group of the formula VIII:

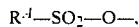

the organic group $R^A$ may suitably be an unsubstituted or substituted hydrocarbon, oxahydrocarbon, thiahydrocarbon or azahydrocarbon group, more especially an alkyl, alkenyl, unsubstituted or substituted aryl (especially phenyl, nitrophenyl, halophenyl or alkylphenyl), unsubstituted or substituted aralkyl (especially benzyl, nitrobenzyl, halobenzyl or alkylbenzyl), unsubstituted or substituted aryloxyalkyl (especially phenoxyalkyl, nitrophenoxyalkyl, halophenoxyalkyl or alkylphenoxyalkyl), or substituted ethyl (especially $R^G$—$CH_2$—$CH_2$—, wherein $R^G$ is defined as below) group.

Examples of groups $R^G$ in the 4"-substituent

include amino, substituted amino, carbamoyl, substituted carbamoyl, sulphamoyl, substituted sulphamoyl, substituted ureido, substituted thioureido, alkoxy, alkythio, optionally substituted aryloxy, optionally substituted arylthio, optionally substituted benzyloxy, optionally substituted benzylthio, substituted suphonyl, substituted sulphinyl, substituted alkyl, substituted alkanoyl, substituted cyano, and other groups more specifically described in U.S. Pat. No. 3,869,445 and U.S. Pat. No. 4,063,014, oc. cit.

Preferably, $R^4$ denotes a hydrocarbon group, particularly a $(C_{1-6})$alkyl group, especially a methyl group.

The present invention includes pharmaceutically acceptable esters, especially in vivo hydrolysable esters, of the compounds of the general formula I. Such esters may be formed at any hydroxy group in the compounds of the general formula I, but usually the ester will be formed at the 2'-hydroxy group of the desosamine ring, thus giving a 2'-O-acyl derivative of the type described in U.S. Pat. No. 2,862,921 (R.E. Booth et al; Upjohn Co.), U.S. Pat. No. 2,993,833 (V.C. Stephens; Eli Lilly), U.S. Pat. No. 3,884,904 (P.H. Jones et al. Abbott Laboratories), U.S. Pat. No. 3,836,519, U.S. Pat. No. 3,842,069, U.S. Pat. No. 3,869,445, US 3,884,903, and U.S. Pat. No. 4,150,220, all op. cit..

Suitable pharmaceutically acceptable in vivo hydrolysable esters include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates.

The present invention also includes acid addition salts, especially pharmaceutically acceptable acid addition salts, of the compounds of the general formula I. Such acid addition salts may, in particular, be formed at the 3'-dimethylamino group of the desosamine ring.

Various acid addition salts of erythromycin are described in U.S. Pat. No. 2,761,859 (C.E. Hoffhine, Jr.; Abbott Laboratories) and U.S. Pat. No. 2,852,429 (J.T. Shepler; Eli Lilly).

Suitable acid addition salts of the compounds of the invention include pharmaceutically acceptable inorganic acid addition salts, for example the sulphate, nitrate, phosphate, borate, hydrochloride and hydrobromide, and also pharmaceutically acceptable organic acid addition salts, for example the acetate, tartrate, maleate, citrate, succinate, benzoate, ascorbate, methane-sulphate, α-keto-glutarate, α-glycerophosphate, and glucose-1-phosphate. Preferably the acid addition salt is the laurylsulphate salt.

Examples of individual compounds according to the present invention include:

(i) erythromycin A 11,12-carbonate 9-oxime (in general formula I, $R^1$ is =NOH; $R^3$ is H; $R^7$ is $CH_3$; $R^8$ is H; $R^9$ is OH);

(ii) erythromycin A 11,12-carbonate 9-methoxime (in general formula I, $R^1$ is =NOCH$_3$; $R^3$ and $R^7$ to $R^9$ as for compound (i));

(iii) 6-O-methylerythromycin A 11,12-carbonate 9-methoxime (in general formula I, $R^3$ is $CH_3$; $R^1$ and $R^7$ to $R^9$ as for compound (ii)) and;

(iv) 6-O-methylerythromycin A 11,12-carbonate 9-ethoxime (in general formula I, $R^1$ is =NOC$_2$H$_5$; $R^3$ and $R^7$ to $R^9$ as for compound (iii));

(v) 6-O-methylerythromycin A 11,12-carbonate 9-oxime (in general formula I, $R^1$ is =NOH; $R^3$ and $R^7$ to $R^9$ as for compound (iii));

(vi) 6-O-methylerythromycin A 11,12-carbonate 9-(2-methoxyethoxymethyl)oxime (in general formula I, $R^1$ is =NOCH$_2$OCH$_2$CH$_2$OCH$_3$; $R^3$ and $R^7$ to $R^9$ as for compound (iii));

(vii) 6-O-methylerythromycin A 11,12-carbonate 9-methoxymethyloxime (in general formula I, $R^1$ is =NOCH$_2$OCH$_3$; $R^3$ and $R^7$ to $R^9$ as for compound (iii));

(viii) erythromycin A 11,12-carbonate 9-ethoxime (in general formula I, $R^1$ is =NOC$_2$H$_5$; $R^3$ and $R^7$ to $R^9$ as for compound (i));

(ix) erythromycin A 11,12-carbonate 9-isopropyloxime (in general formula I, $R^1$ is =NOCH(CH$_3$)$_2$; $R^3$ and $R^7$ to $R^9$ as for compound (i));

(x) erythromycin A 11,12-carbonate 9-carbamoylmethyloxime (in general formula I, $R^1$ is =NOCH$_2$CONH$_2$; $R^3$ and $R^7$ to $R^9$ as for compound (i));

(xi) erythromycin A 11,12-carbonate 9-methoxymethyloxime (in general formula I, $R^1$ is =NOCH$_2$OCH$_3$; $R^3$ and $R^7$ to $R^9$ as for compound (i));

(xii) erythromycin A 11,12-carbonate 9-(2-methoxyethoxymethyl)oxime (in general formula I, $R^1$ is =NOCH$_2$CH$_2$OCH$_3$; $R^3$ and $R^7$ to $R^9$ as for compound (i));

(xiii) erythromycin A 11,12-carbonate 9-(2-hydroxyethyl)oxime methoxymethyloxime (in general formula I, $R^1$ is =NOCH$_2$CH$_2$OH; $R^3$ and $R^7$ to $R^9$ as for compound (i));

(xiv) erythromycin A 11,12-carbonate-9-(2-keto-1pyrrolidinylmethyl)oxime (in general formula I, $R^1$ is =NOCH$_2$NC$_4$H$_6$O; $R^3$ and $R^7$ to $R^9$ as for compound (i));

(xv) erythromycin A 11,12-carbonate-9-prop-2enyloxime (in general formula I, $R^1$ is =NOCH$_2$CHCH$_2$; $R^3$ and $R^7$ to $R^9$ as for compound (i));

(xvi) erythromycin A 11,12-carbonate-9-n-propyloxime (in general formula I, $R^1$ is =NOCH$_2$CH$_2$CH$_3$; $R^3$ and $R^7$ to $R^9$ as for compound (i));

(xvii) erythromycin A 11,12-carbonate-9ethoxymethyloxime (in general formula I, $R^1$ is =NOCH$_2$OCH$_2$CH$_3$; $R^3$ and $R^7$ to $R^9$ as for compound (i));

(xviii) erythromycin A 11,12-carbonate-9-(2-dimethylaminoethyl)oxime (in general formula I, $R^1$ is =NOCH$_2$CH$_2$N(CH$_3$)$_2$; $R^3$ and $R^7$ to $R^9$ as for compound (i));

(xix) erythromycin A 11,12-carbonate-9-methylthiomethoxime (in general formula I, $R^1$ is =NOCH$_2$SCH$_3$; $R^3$ and $R^7$ to $R^9$ as for compound (i));

(xx) erythromycin A 11,12-carbonate-9cyclopentyloxime (in general formula I, $R^1$ is =NOC$_5$H$_{10}$; $R^3$ and $R^7$ to $R^9$ as for compound (i));

(xxi) erythromycin A 11,12-carbonate-9-(2-methylprop-2-enyl)-oxime (in general formula I, $R^1$ is =NOCH$_2$C(CH$_3$)CH$_2$; $R^3$ and $R^7$ to $R^9$ as for compound (i));

(xxii) erythromycin A 11,12-carbonate-9-(2-methylpropyl)oxime (in general formula I, $R^1$ is =NOCH$_2$CH(CH$_3$)$_2$; $R^3$ and $R^7$ to $R^9$ as for compound (i));

(xxiii) erythromycin A 11,12-carbonate-9-(2-oxopropyl)oxime (in general formula I, $R^1$ is =NOCH$_2$COCH$_3$; $R^3$ and $R^7$ to $R^9$ as for compound (i));

(xxiv) erythromycin A 11,12-carbonate-9- dimethylcarbamoyl-methoxime (in general formula I, $R^1$ is =NOCH$_2$CON(CH$_3$)$_2$; $R^3$ and $R^7$ to $R^9$ as for compound (i));

(xxv) erythromycin A 11,12-carbonate-9-(2-methoxyethyl)oxime (in general formula I, $R^1$ is =NOCH$_2$CH$_2$OCH$_3$; $R^3$ and $R^7$ to $R^9$ as for compound (i));

(xxvi) erythromycin A 11,12-carbonate-9-methoxycarbonyl methyl-oxime (in general formula I, $R^1$ is =NOCH$_2$CO$_2$CH$_3$; $R^3$ and $R^7$ to $R^9$ as for compound (i));

(xxvii) erythromycin A 11,12-carbonate-9-(2-pyridyl) methyloxime (in general formula I, $R^1$ is $=NCH_2C_5H_4N$; $R^3$ and $R^7$ to $R^9$ as for compound (i));

as well as corresponding derivatives in which the 4″-position is modified as discussed above;

and also pharmaceutically acceptable esters and acid addition salts of such compounds.

The erythromycin 9-(optionally substituted)oxime 11,12-carbonate derivatives according to the invention may be prepared by reacting an erythromycin A 9-oxime or 9-substituted-oxime having free hydroxy substituents at the 11- and 12-positions, in which any reactive groups (other than the 11- and 12-hydroxy groups) may optionally be protected, with a reactive carbonyl compound; and thereafter if necessary carrying out one or more of the following steps in any suitable order:

(a) converting a substituent on the erythromycin structure to another such substituent in a conventional manner;
(b) removing any protecting groups; and
(c) forming a pharmaceutically acceptable ester or acid addition salt.

A suitable resulting 9-substituted-oxime (for example a 9-acyloxime) compound according to the invention may, if desired, subsequently be converted to a 9-oxime compound according to the invention.

A resulting 9-oxime compound according to the invention may, if desired, be converted to a 9-substituted-oxime or 9-imino compound according to the invention.

More particularly, a compound of the general formula I as hereinbefore defined or a pharmaceutically acceptable ester or acid addition salt thereof may be prepared by a process which comprises reacting a compound of the general formula X:

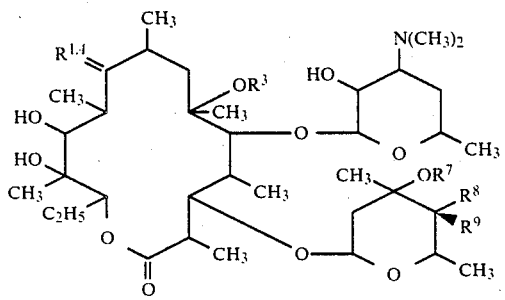

wherein
$R^{1,4}$ denotes an oxime or substituted oxime group, and
$R^3$, $R^7$, $R^8$ and $R^9$ are defined as above with respect to general formula I, in which compound of the general formula X any reactive group (other than the 11- and 12-hydroxy groups) may optionally be protected,
with a reactive carbonyl compound
to give a compound of the general formula I in which
$R^1$ denotes an oxime or substituted oxime group;
and thereafter, if necessary or desired, carrying out one or more of the following steps in any suitable order:
(a) converting a substituted oxime group denoted by $R^1$ to another substituted oxime group or to an oxime group;
(b) converting an oxime group denoted by $R^1$ to a substituted oxime group, or to an imino group;
(c) converting any one or more of the groups denoted by $R^3$, $R^8$ and $R^9$ to another such group;
(d) removing any protecting group that may be present; and
(e) forming a pharmaceutically acceptable ester or acid addition salt.

A compound of the general formula X in which:
each of $R^3$ and $R^8$ denotes hydrogen,
$R^7$ denotes methyl, and
$R^9$ denotes hydroxy,
is erythromycin A 9-oxime or a 9-substituted-oxime derivative thereof, which may be prepared from erythromycin A by known methods, for example by the methods described in the above-cited references relating to erythromycin 9-oximes and 9-substituted-oximes.

Compounds of the general formula X in which $R^3$ denotes an alkyl group may be prepared by the methods described in the respective references cited above.

Other compounds of the general formula X may also be prepared, by methods known per se, from erythromycin A or the corresponding 9-oxime or 9-substituted-oxime derivative. For example, a compound in which the 4″-position is substituted other than as in naturally-occurring erythromycin A (that is to say, in which $R^8$ is other than hydrogen and/or $R^9$ is other than hydroxy) may be prepared as described in the respective references cited above.

In general, in the preparation of 9-oxime and 9-substituted-oxime compounds of the general formula X from erythromycin A, the conversion of the 9-oxo group of erythromycin A to a 9-oxime or 9-substituted-oxime group may be effected prior to or subsequent to modification of other positions of the erythromycin molecule.

Prior to carrying out the reaction of a compound of the general formula X with the reactive carbonyl compound, any reactive group of a compound of the general formula X (other than the 11- and 12-hydroxy group) may optionally be protected.

For example, the 3′-dimethylamino group may, if desired, be protected by means of an N-protecting group in known manner, for example by the method described by E.H. Flynn et al, (*J. Amer. Chem. Soc.*, 1955, 77, 3104–3106).

Examples of suitable N-protecting groups include benzyloxycarbonyl, and substituted benzyloxycarbonyl, (for example, p-methylbenzyloxycarbonyl, p-nitrobenzyloxycarbonyl, p-bromobenzyloxycarbonyl, p-phenylazobenzyloxycarbonyl, and p-(p′-methoxyphenylazo)-benzyloxycarbonyl). A preferred N-protecting group is benzyloxycarbonyl.

It may also be advantageous to protect one or more of the hydroxy groups present in the erythromycin molecule (other than the 11- and 12-hydroxy groups) prior to the reaction. In particular, it may be advantageous to protect any hydroxy groups present at the 2′- and 4″-positions.

It is convenient to employ the same group to protect the 2′-hydroxy group as that employed to protect the amino moiety, especially a benzyloxycarbonyl group.

The 4″-hydroxy group may be protected by acylation in known manner, for example by the method described in Jones et al. *J. Med. Chem.*, 1972, 15, 631. A preferred acyl group for this purpose is the formyl group, which can subsequently readily be removed by hydrolysis.

The 2′-hydroxy group may, if desired, conveniently also be protected by acylation simultaneously with the protection of the 4″-hydroxy group, although it may be convenient to protect the 2'-hydroxy group simultaneously with protection of the 3'-dimethylamino groups discussed above.

In the event that an erythromycin 9-oxime compound according to the invention is desired, it may in some cases be advantageous to use an erythromycin 9-substituted-oxime compound of the general formula X in which the oxime substituent is a protecting group which can readily be removed after completion of the reaction with the carbonyl compound. Suitable oxime-protecting groups are known in the art and include, for example, the N-protecting groups listed above. If the 3'-dimethylamino group is being protected, it may be convenient to protect the oxime group simultaneously therewith, suitably using a benzyloxycarbonyl group.

Any reactive substituents that may be present in the group $R^8$ or $R^9$ should preferably also be protected in a conventional manner.

In the process according to the invention, the erythromycin compound of the general formula X, optionally containing protective groups, is reacted with a reactive carbonyl compound.

Examples of suitable reactive carbonyl compounds for use in the process according to the invention include phosgene $COCl_2$; oxalyl chloride $(COCl)_2$; carbonyl di-imidazole

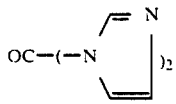

and certain isocyanates.

Suitable isocyanates include in particular aryl isocyanates, ArNCO (where Ar denotes an aryl group), which should preferably carry an electron-withdrawing substitutent on the aryl moiety. Examples of such compounds include nitrophenylisocyanates and methylsulphonylphenylisocyanates.

Also suitable, provided that the 6-hydroxy group is blocked (i.e. $R^3$ denotes alkyl) or is protected, are acyl isocyanates of the formula

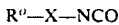

in which $R^o$ denotes the residue of an organic acid of the formula

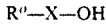

and X denotes —CO— or —SO$_2$—.

Examples of such organic acids include acetic acid, methoxyacetic acid, trichloroacetic acid, benzoic acid, and p-toluenesulphonic acid.

The reactive carbonyl compound may suitably be used in an excess of from 1 to 10 equivalents, based on the erythromycin compound.

The reactivity of the various reactive carbonyl compounds does vary and it is necessary to choose the reaction conditions accordingly.

In the case of the more reactive carbonyl compounds, phosgene, oxalyl chloride and acyl isocyanates, for example, the reaction may conveniently be carried out at a temperature within the range of from −50° to +50° C., preferably from −20° to +30° C., in an inert solvent. In the case of phosgene and oxalyl chloride, the reaction is preferably carried out in the presence of a weak base (e.g. triethylamine) as an acid acceptor: the presence of a catalytic amount of, for example, dimethylaminopyridine can also be advantageous.

In the case of other reactive carbonyl compounds, carbonyl di-imidazole and the aryl isocyanates, for example, the reaction may conveniently be carried out at a temperature of from 0° to 150° C., preferably from 30° to 100° C., in an inert solvent. The reaction using carbonyl di-imidazole should preferably be carried out in the presence of a strong base, for example sodium hydride, which may conveniently be used in an amount of, say 2 equivalents (based on the erythromycin compound).

Suitable inert solvents for the reaction include, for example, dichloromethane, chloroform, diethyl ether, tetrahydrofuran, dioxane, and dimethoxyethane (although the lower boiling solvents will not, of course, be suitable in cases where the reaction is carried out at higher temperatures).

With certain reagents, if the 4''-position has been left unprotected, substitution may occur at that position; for example, when using carbonyl di-imidazole, substitution of an imidazoylcarbonyl group can occur on the 4''-O-atom. Any such substituent may, if desired, readily be removed by displacement by an alcohol. For example, displacement by benzyl alcohol will give a 4''-benzyl carbonate derivative, and the 4''-hydroxy group may then be restored by hydrogenation in the manner discussed below. Alternatively, displacement by dihydric alcohol, for example, ethylene glycol can restore the 4''-hydroxy group directly.

If the initial erythromycin compound of the general formula X contains a 9-oxime group, that group may react with the carbonyl compound to form a 9-substituted-oxime, but again the substituent group may become removed during later reaction steps to leave the 9-oxime. Alternatively, the 9-oxime group may first be protected, for example as discussed above, so that the reaction is in fact carried out on a 9-substituted-oxime.

After completion of the reaction with the carbonyl compound, the 9-oxime or 9-substituted-oxime group may optionally be converted into another such group. If the desired product of the general formula I contains a 9-imino group, it may be obtained by conversion from a 9-oxime group.

All such conversions at the 9-position may be carried out in known manner, for example as described in the above-cited references. For example, the oxime may be converted to the imine by reaction with titanium trichloride in known manner.

Also after completion of the reaction with the carbonyl compound, and prior or subsequent to any conversion of the 9-substituent, the group(s) $R^8$ and $R^9$ may be converted to any of the other such groups within the definitions given above by methods known in the art, for example by the methods disclosed in the above-cited references. For example, a compound in which $R^9$ denotes hydrogen and $R^8$ denotes hydroxy can be converted to a compound in which $R^8$ and $R^9$ together denote oxo and optionally thereafter to a compound in which $R^9$ denotes hydroxy or acetoxy and $R^8$ denotes hydrogen by methods analogous to those described in U.S. Pat. No. 3,884,903, op. cit..

After completion of the reaction with the carbonyl compound and the optional subsequent hydrolysis, any remaining protecting groups (such as a benzyloxycarbonyl group) may be removed by a conventional method. It is often appropriate to employ a hydrogenation procedure.

The hydrogenation may suitably be carried out in the presence of a transition metal catalyst, for example palladium, which may, for example, be in the form of palladium on carbon (charcoal), palladium on barium sulphate, palladium on calcium carbonate, or palladium black. A favoured catalyst is palladium on carbon (sometimes referred to as palladium on charcoal); for example 5%, 10%, 20% or 30% palladium on carbon. A low, medium or high pressure of hydrogen may be used in this reaction, for example a pressure of from 1 to 6 atmospheres absolute, a pressure of 1 atmosphere absolute being convenient. The reaction may suitably be carried out at a non-extreme temperature, for example at a temperature within the range of from 0° C. to 30° C., preferably from 12° C. to 25° C. It is generally convenient to carry out the reaction at ambient temperature. The reaction is preferably carried out at a pH within the range of from 4.5 to 5.0, which may be maintained by the use of a suitable buffer, for example an acetate buffer at pH 4.8. Suitable solvents for carrying out the hydrogenation include ethanol, n-propanol, isopropanol, tetrahydrofuran, dioxan, ethyl acetate, a mixture of two or more such solvents, or such a solvent or mixture in the presence of water. A favoured solvent is ethanol.

When necessary, the dimethylamino group at the 3'-position may conveniently be restored by effecting a reductive methylation, which advantageously may be carried out at the same time as the reductive removal of the protecting groups, as in the method of Flynn et al, op. cit..

A compound of the general formula I may be converted to a pharmaceutically acceptable salt thereof or ester thereof in a conventional manner at any convenient stage in the manufacturing process, for example before or after the removal of any protecting groups and/or before or after any conversion of the 9-substituent and/or of groups $R^8$ and $R^9$ to other such groups.

Isolation and purification of a compound according to the invention may be carried out using conventional methods, and may include a chromatography step. Preferably the product is isolated in crystalline form.

The compounds according to the invention, that is to say, the compounds of the general formula I and their pharmaceutically acceptable salts and esters, have antibacterial properties and are useful for the treatment of bacterial infections in animals, especially mammals, including humans, in particular humans and domesticated animals (including farm animals). The compounds may be used for the treatment of infections caused by a wide range of gram-positive and gram-negative organisms including, for example, *Bacillus subtilis, Corynebacterium xerosis, Sarcina lutea, Staphylococcus aureus, Streptococcus faecalis, Streptococcus pyogenes, Streptococcus agalactiae, Streptococcus pneumoniae*, Haemophilus sp. Neisseria sp., Chlamydia sp., and Legionella sp..

The present invention provides a pharmaceutical composition comprising a compound according to the invention together with a pharmaceutically acceptable carrier or excipient.

The present invention also provides a method of treating bacterial infections in animals, especially in humans and in domesticated mammals, which comprises administering a compound or composition according to the invention to a patient in need thereof.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colouring agents.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.5 to 50 mg/kg of body weight. For an adult human (of approximately 70 kg body weight), from 100 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferably from 50 to 500 mg, of a compound according to the invention.

No adverse toxicological effects are indicated when the compounds according to the invention are administered within the above-mentioned dosage ranges.

The following examples illustrate the preparation of compounds according to the present invention. The percentage yields quoted throughout the examples are calculated on the theoretical yield from the corresponding erythromycin derivative used as the respective starting material.

EXAMPLE 1

N,2'-O-Dibenzyloxycarbonyl-N-desmethylerythromycin A 11,12-carbonate 9-oxime (2)

EXAMPLE 1a

4"-O-formyl-2'-O,N-dibenzyloxycarbonyl-N-desmethylerythromycin erythromycin A 9-benzyloxycarbonyloxime (1)

To a solution of N-desmethyl-N,2'-O-dibenzyloxycarbonylerythromycin A 9-benzyloxycarbonyloxime (10 g) (obtained from erythromycin A 9-oxime by treatment with benzyl chloroformate in the manner of E.H.-Flynn et al, *J.Amer.Chem.Soc.*, 1955, 77, 3104–3106) and 4-dimethylaminopyridine (100 mg) in pyridine (50 ml) and ether (100 ml) was added acetic-formic anhydride (10 ml) over one hour at 0° C.; then the cooling bath was removed and the mixture was stirred at room temperature for 5½h. The mixture was then worked up by addition of excess aqueous sodium hydrogen carbonate solution, evaporation to low bulk in vacuo at room temperature and partitioning the residue between ethyl acetate and water. The ethyl acetate layer was dried (MgSO₄) and evaporated.

The crude residue was then chromatographed on silica gel, eluting with ethyl acetate/hexane mixture 40/60.

In this way two chromatographically pure fractions were obtained.

The less polar fraction, eluted first, was the desired 4"-O-formyl compound (1), an amorphous solid (2.7 g, 26%) $\nu_{max}$ (CHCl₃) 1750 (sh), 1730, 1690. (Found: m/e 1165 MH$^+$, calc. MW 1164; C, 63.05; H, 7.25; $C_{61}H_{85}N_3O_{19}$ requires C, 62.89; H, 7.22; N, 2.41).

EXAMPLE 1b

N,2'-O-Dibenzyloxycarbonyl-N-desmethylerythromycin A 11,12-carbonate 9-oxime (2)

To a solution of 4"-O-formyl-2'-O,N-dibenzyloxycarbonyl-N-desmethylerythromycin A 9-benzyloxycarbonyloxime (1) (500 mg) in dichloromethane (10 ml) and triethylamine (5 ml) containing 4-dimethylaminopyridine (50 mg) at −30° C. was added a 12.5% solution of phosgene in toluene (4 ml, 4.4 eq.) and the mixture was allowed to reach 20° C. over 1 h. After stirring for 18 h, methanol (5 ml) was added and the mixture was evaporated. The residue was partitioned between ethyl acetate and aqueous sodium hydrogen carbonate, the organic layer separated, washed with dilute aqueous citric acid, and evaporated. The residue was then dissolved in methanol/triethylamine/water (100/4/10) (15 ml) and kept for 18 h at 20° C. This solution was then evaporated in vacuo to low bulk and the residue partitioned between ethyl acetate and water. The organic layer was separated, washed with aqueous sodium hydrogen carbonate, dried (MgSO₄) and evaporated. The residue was then chromatographed on silica gel, eluting with ethyl acetate/hexane. From this was obtained the desired compound (2) (100 mg), followed by unreacted N,2'-O-dibenzyloxycarbonyl-N-desmethyl-erythromycin A oxime (3) (100 mg).

EXAMPLE 2

N,2'-O-Dibenzyloxycarbonyl-N-desmethylerythromycin A 11,12-carbonate 9-oxime (2)

4"-O-Formyl-2'-O,N-dibenzyloxycarbonyl-N-desmethylerythromycin A 9-benzyloxycarbonyloxime (1) (0.6 g), 4-dimethylaminopyridine (100 mg) and triethylamine (0.9 ml) in dry tetrahydrofuran (10 ml) was cooled to −25° C. under dry nitrogen, and oxalyl chloride (0 13 ml) was added dropwise with stirring. The reaction was allowed to warm to +20° C. over 3 h, and stirred at this temperature for a further 2 h. The reaction mixture was diluted with ether (50 ml) and washed with water (20 ml), 10% aqueous citric acid (20 ml), and saturated aqueous sodium bicarbonate (20 ml). After drying with magnesium sulphate and concentration by evaporation under reduced pressure, the crude product was purified by chromatography on silica gel using 20% diethyl ether in dichloromethane as eluent, to give 4"-O-formyl-2'-O,N-dibenzyloxycarbonyl-N-desmethyl-erythromycin A 11,12-carbonate 9-benzyloxycarbonyloxime (5) (0.23 g) and recovered starting material (1) (0.23 g). Hydrolysis of this product with methanol/triethylamine/water mixture as described in Example 1 gave N,2'-O-dibenzyloxycarbonyl-N-desmethylerythromycin A 11,12-carbonate 9-oxime (2).

EXAMPLE 3

4"-O-Formyl-2'-O,N-dibenzyloxycarbonyl-N-desmethylerythromycin erythromycin A 11,12-carbonate 9-benzyloxycarbonyloxime (5)

4"-O-Formyl-2"-O,N-dibenzyloxycarbonyl-N-desmethylerythromycin A 9-benzyloxycarbonyloxime (1), (0.3 g) in dry tetrahydrofuran (5 ml) was treated with p-nitrophenylisocyanate (0.12 g) at reflux for 3 h. The reaction mixture was cooled, filtered and evaporated and the residue was purified by chromatography on silica gel eluting with dichloromethane/diethyl ether mixtures to give, in addition to recovered starting material (1) (100 mg), the title compound (5) (120 mg) $\nu_{max}$ (CHCl3) 1800, 1730, 1690 cm$^{-1}$ m.s. (FAB) 1213 (MNa$^+$).

EXAMPLE 4

Erythromycin A 11,12-carbonate 9-oxime (4)

N,2'-0-Dibenzyloxycarbonyl-N-desmethylerythromycin A 11,12-carbonate 9-oxime (2) (120 mg) in ethanol (15 ml) and pH 4.8 acetate buffer (1.5 ml) was hydrogenated at atmospheric pressure and room temperature over 10% Pd/C (30 mg) for 1 h. Aqueous formaldehyde (40%) (0.25 ml) was then added and hydrogenation was continued for 1 h. The solution was then filtered, made alkaline with aqueous sodium hydrogen carbonate, and evaporated to low bulk in vacuo. The residue was partitioned between ethyl acetate and water and the organic layer was separated, dried (MgSO₄) and evaporated. The residue was then purified by chromatography on silica gel eluting with dichloromethane/methanol/0.880 ammonia (200/10/1). The major product (62 mg) was the desired title compound, an amorphous white solid: $\nu_{max}$ (CHCl₃) 3550, 1800, 1730, 1600 (W) 1450 cm$^{-1}$ [α]D$^{20}$(1% in CHCl₃) −24.3°. Found: FAB m.s. MNa$^+$797.

EXAMPLE 5a

2'-O,4"-O,N-Tris(benzyloxycarbonyl)-des-N-methylerythromycin erythromycin 9-methoxime 11,12-carbonate (7)

2'-O,N-Dibenzyloxycarbonyl-des-N-methylerythromycin 9-methoxime (6) (500 mg) (EP 0 201 166 A 1 (Beecham) Preparation 1) in dry tetrahydrofuran (10 ml) was treated with 50% sodium hydride dispersion in oil (50 mg) and the mixture was stirred for 5 minutes. Carbonyl diimidazole (300 mg) was added and the mixture was stirred at 60° C. for 30 minutes. The mixture was cooled to room temperature and benzyl alcohol (0.5 ml) was added and stirring was continued for 30 minutes. The mixture was diluted with ethyl acetate (50 ml) and the solution was washed with dilute sodium hydrogen carbonate solution (30 ml), water (30 ml), diluted HCl (30 ml) and water (30 ml). The solution was dried (sodium sulphate) and the solvent was removed by evaporation under reduced pressure to yield a colourless oil. The oil was chromatographed on silica gel using ethyl acetate-hexane as eluant to give the title compound (7) as a colourless gum (410 mg), $[\alpha]D^{20} = -44.3°$ (1% solution in CHCl$_3$). $\nu_{max}$ (CHCl$_3$) 3500, 1795, 1735, and 1685 cm$^{-1}$; FAB m.s. 1199 (MNa+).

EXAMPLE 5b

Erythromycin 11,12-carbonate 9-methoxime (8)

2'-O,4"-O,N-Tris(benzyloxycarbonyl)-des-N-methylerythromycin 9-methoxime 11,12-carbonate (7) (150 mg) was dissolved in ethanol (12 ml) and acetate buffer (1 ml; pH 4.8) was added. The solution was shaken with 10% palladium-charcoal (50 mg) under hydrogen (1 atmosphere) for 30 minutes. 37% Formaldehyde solution (0.6 ml) was added and the hydrogenation was continued for a further 1.5 hours. The catalyst was removed by filtration and was washed with ethanol and water. The ethanol was evaporated from the filtrate under reduced pressure, and the resulting residue was diluted with water and basified (pH 11) by adding solid potassium carbonate. The mixture was extracted with ethyl acetate (2 × 30 ml) and the combined extracts were washed with water (30 ml) and dried (sodium sulphate) The solvent was evaporated under reduced pressure to give the title compound (8) as a colourless gum (100 mg), $[\alpha]D^{20} = -20.1°$ (1% solution in CHCl$_3$); $\nu_{max}$ (CHCl$_3$) 3550, 3450, 1795 and 1730 cm$^{-1}$; FAB m.s. 811 (MNa+).

EXAMPLE 6a

2'-O,N-Dibenzyloxycarbonyl-6-O-methyl-4"-O-(N-imidazolylcarbonyl)-des-N-methylerythromycin A 11,12-carbonate 9-methoxime (10)

2'-O,N-Dibenzyloxycarbonyl-6-O-methyl-des-N-methylerythromycin A 9-methoxime (9) (EP 0 158 467 A2, Taisho, Example 16) (500 mg) in tetrahydrofuran (15 ml) was stirred with 50% sodium hydride dispersion in oil (50 mg) for 10 min. Carbonyl di-imidazole (400 mg) was then added and the mixture was refluxed for 1.25 h. It was then cooled, a little water was added and the tetrahydrofuran was evaporated off in vacuo. The residue was partitioned between ethyl acetate and water then the organic layer was further washed with aqueous citric acid and sodium hydrogen carbonate solution then dried (MgSO$_4$) and evaporated. The residue was purified by chromatography on silica gel, eluting with ethyl acetate/hexane (1/1) to give the title compound (10) as an amorphous solid (439 mg) $\nu_{max}$ (CHCl$_3$) 1795, 1760, 1740, 1690, 1460 cm$^{-1}$ FAB m.s. 1151 MH$^-$.

EXAMPLE 6b

2'-O,4"-O,N-Tris(benzyloxycarbonyl)-6-O-methyl-des-N-methylerythromycin A 11,12-carbonate 9-methoxime (11) and 2'-O,N-dibenzyloxycarbonyl-6-O-methyl-des-N-methylerythromycin erythromycin A 11,12-carbonate 9-methoxime (12)

2'-O,N-Dibenzyloxycarbonyl-6-O-methyl-4"-O-(N-imidazoylcarbonyl)-des-N-methylerythromycin A 11,12-carbonate 9-methoxime (10) (296 mg) was mixed in tetrahydrofuran (5 ml) with benzyl alcohol (0.5 ml) and 50% sodium hydride dispersion in oil (10 mg). After stirring for 1.5 h. at 20° C. a little water was added. tetrahydrofuran was removed by evaporation and the residue was dissolved in ethyl acetate and washed with dilute citric acid and then brine. The solution was dried (MgSO$_4$) and evaporated and the residue chromatographed on silica gel eluting with ethyl acetate/hexane (1/1). In this way was obtained the desired tris-benzyloxycarbonyl compound (11) (161 mg) as an amorphous solid $\nu_{max}$ (CHCl$_3$) 1790, 1730, 1720 (sh), 1690, 1450 cm$^{-1}$ and a more polar dibenzyloxycarbonyl compound (12) (56 mg) $\nu_{max}$ (CHCl$_3$) 3500 (b), 1790, 1730, 1685, 1450 Cm$^{-1}$.

EXAMPLE 6c

6-O-Methylerythromycin A 11,12-carbonate 9-methoxime (13)

A mixture of 2'-O,4"-O,N-Tris(benzyloxycarbonyl)-6-O-methyl-des-N-methylerythromycin A 11,12-carbonate 9-methoxime (11) and 2'-O,N-bis(benzyloxycarbonyl)-6-O-methyl-des-N-methyl-erythromycin A 11,12-carbonate 9-methoxime (12) (total 312 mg) was treated as in the method of Example 4 to give the title compound (13) (130 mg) as an amorphous solid after chromatography on silica gel eluting with dichloromethane/methanol/0.880 ammonia (200/10/1), $\nu_{max}$ (CHCl$_3$) 3530, 3450 (b), 1790, 1730, 1455 cm$^{-1}$ $[\alpha]^{20}_D -64.4°$, FAB m.s. 802 M+.

EXAMPLE 7

6-O-Methylerythromycin A 11,12-carbonate 9-ethoxime (14)

2,'-O,N-Dibenzyloxycarbonyl-6-O-methyl-des-N-methyl-erythromycin A 9-ethoxime (13) (EP 0 158 467 A2, Taisho, Example 17) (560 mg) in tetrahydrofuran (10 ml) was treated with sodium hydride and carbonyl di-imidazole as in Example 6a. The reaction product was not chromatographed but was then treated with benzyl alcohol/sodium hydride as in Example 6b. This product was not chromatographed but was then hydrogenated and treated with formaldehyde as in Example 4 to give, after chromatography on silica gel, the title compound (14) (120 mg) $\nu_{max}$ (CHCl$_3$) 3570, 3400 (b), 1790, 1730, 1450 cm$^{-1}$ $[\alpha]_D 20 -50.2°$ FAB m.s. MNa+839.

EXAMPLE 8

6-O-methylerythromycin A 11,12-carbonate 9-oxime (17)

A solution of 6-O-methyl-2'-O,3'-N-bis(benzyloxycarbonyl)-N-desmethylerythromycin A 9-O-(o-chlorobenzyl)oxime (16), (EP 0 180 415 A2, Taisho, Example 26) (500 mg) in tetrahydrofuran (10 ml) was treated with 50% sodium hydride suspension in oil (30 mg) for 10 min at 20° C. Carbonyl di-imidazole (320 mg) was added and the mixture was refluxed for 1.5 h. It was then cooled, benzyl alcohol (1 ml) was added, then stirring was maintained for 1.5 h at room temperature. The mixture was diluted with ethyl acetate and washed with water, dried (MgSO$_4$) and evaporated in vacuo. The above residue was dissolved in a mixture of methanol (15 ml) water (0.5 ml) and acetic acid (0.5 ml), palladium black (100 mg) was added, and the mixture was hydrogenated at atmospheric pressure for 7 h at 20° C. After filtration the mixture was made alkaline with aqueous sodium hydrogen carbonate and evaporated to low bulk in vacuo. The residue was dissolved in ethyl acetate, washed with aqueous sodium hydrogen carbonate, dried (MgSO$_4$), and evaporated to dryness in vacuo. This residue was redissolved in ethanol (15 ml), pH 4.8 acetate buffer (1.5 ml) and 40% aqueous formaldehyde (0.5 ml) then hydrogenated as in the method of Example 4 to give, after chromatography, 6-O-methylerythromycin A 11,12-carbonate 9-oxime (17, 147 mg) $[\alpha]_D20 = -38.6°$ (1% solution in CHCl$_3$) $\nu_{max}$ (CHCl$_3$) 3550, 3300(b), 1800, 1730, 1450 cm$^{-1}$. FAB m.s. 811 (MNa$^+$).

EXAMPLE 9

6-O-Methylerythromycin A 11,12-carbonate 9-oxime (17)

As in Example 8, a solution of 6-O-methyl-2'-O,3'-N-bis(benzyloxycarbonyl)-N-desmethylerythromycin A 9-O-(o-chlorobenzyl)oxime (16) (1.14g) in tetrahydrofuran (20ml) was treated with 50% sodium hydride suspension in oil (138mg) for 10 min at 20° C. Carbonyl di-imidazole, (735mg) was added and the mixture was refluxed for 1.5h. To the cooled mixture was then added ethylene glycol (1ml) and N/1 sodium hydroxide solution (0.2ml). After stirring for 1h tetrahydrofuran was evaporated off and the residue was dissolved in ethyl acetate and washed with dilute citric acid and then brine. The solution was dried (MgSO$_4$) and evaporated and the residue chromatogaphed on silica gel eluting with ethyl acetate/hexane (1/1). In this way was obtained 6-O-methyl-2'-O,3'-N-bis(benzyloxy-carbonyl)-N-desmethylerythromycin A 11,12-carbonate 9-O-(o-chlorobenzyl)oxime (18) (932mg) $\nu_{max}$ (CHCl$_3$) 3550(w), 1790, 1740, 1690, 1450 cm$^{-1}$, FAB m.s. MNa$^+$1189.

The product (18) (400mg) in methanol (5ml) was treated with 10% Pd/C (100mg), formic acid (0.2ml) and sodium formate (40mg) under nitrogen for 2 h at 20° C. The reaction mixture was made alkaline with aqueous sodium hydrogen carbonate, methanol was evaporated off and the residue was dissolved in ethyl acetate and washed with water then dried and evaporated to give 6-O-methyl-N-desmethylerythromycin A 11,12-carbonate 9-oxime (19) (276mg) $\nu_{max}$ (CHCl$_3$) 3550, 3250(b), 1795, 1735, 1450 cm$^{-1}$.

Compound (19) (500mg) in ethanol (20ml) and pH 4.8 acetate buffer (2ml) was treated with aqueous formaldehyde (38%, 0.5ml) and was then hydrogenated at atmospheric pressure over 10% Pd/C (75ml) for 1 h and the product was then purified as in Example 4 to give the title compound (434mg) identical (i.r., n.m.r.) with compound (17) obtained in Example 8.

EXAMPLE 10

6-0-Methylerythromycin A 11,12-carbonate 9-O-(2-methoxyethoxymethyl)oxime (23)

Treatment of 2'-O,3'-N-bis(benzyloxycarbonyl-N-desmethyl-6-O-methylerythromcyin A 9-O-(2-methoxyethoxymethyl)oxime (20) (EP 0 158 467 A2, Taisho, Example 36) by the method of Example 6a gave 2'-O,3'-N-bis(benzyloxycarbonyl)-N-desmethyl-4"-O-(N-imidazolylcarbonyl)-6-O-methylerythromycin A 11,12-carbonate 9-O-(2-methoxyethoxymethyl)oxime (21) which was treated with ethylene glycol/sodium hydroxide as in Example 9 to yield 2'-O,3'-N-bis(benzyloxy-carbonyl)-N-desmethyl- 6-O-methylerythromycin A 11,12-carbonate 9-O-(2- methoxyethoxymethyl)oxime (22). Compound (22) was then treated as in Example 4 to give the title compound as a white amorphous solid (23) $\nu_{max}$ (CHCl$_3$) 1790, 1730, 1450 cm$^{-1}$ $[\alpha]^{20}D$ 45.4° (1% CHCl$_3$) e.i. m.s. MH$^-$877.

EXAMPLE 11

6-O-Methylerythromycin A 11,12-carbonate 9-O-(methoxymethyl)oxime (27)

Reaction of 2'-O,3'-N-bis(benzyloxycarbonyl)-N-desmethyl-6-0-methyl-erythromycin A 9-O-(methoxymethyl)oxime (24) (EP 0 158 467 A2, Taisho, Example 20) as described in Example 10 gave successively 2'-O,3'-N-bis(benzyloxycarbonyl)-N-desmethyl-4"-O-(N-imidazolyl-carbonyl)-6-O-methylerythromycin A 11,12-carbonate 9-O-(methoxymethyl)oxime (25), 2'-O,3'-N-bis (benzyloxycarbonyl-N-desmethyl-6-O-methylerythromycin A 11,12-carbonate 9-O-(methoxymethyl)oxime (26), and finally the title compound (27) as a white amorphous compound $\nu_{max}$ (CHl$_3$) 1790, 1730 cm$^{-1}$ $[\alpha]^{20}D$ (1% CHCl$_3$) -47.4°.

EXAMPLE 12

Erythromycin A 11,12-carbonate 9-oxime (4)

To N,2'-O-dibenzyloxycarbonyl-N-desmethylerythromycin A 9-benzyloxycarbonyloxime (1.14g) (see Example 1a) in dry dichloromethane (10ml) was added dry pyridine (0.8ml). The mixture was cooled in ice, and phosgene (3.5ml of a 12.5% w/w solution in toluene) was added. The mixture was allowed to warm to room temperature and stirred for 100 minutes. Benzyl alcohol (0.8 ml) was added and the mixture stirred for a further 1h. The reaction mixture was then diluted with chloroform and washed with water, dilute citric acid and saturated sodium bicarbonate. After drying (magnesium sulphate) and evaporation, the residue was taken up in 90:10:4 methanol/water/ triethylamine (30ml) and allowed to stand at room temperature for 4h. The reaction mixture was then concentrated by evaporation at reduced pressure, taken up in ethyl acetate and worked up as above. After chromatography (30–40% ethyl acetate in hexane) N,2'-O,4"-O-tribenzyloxycarbonyl-N-desmethylerythromycin A 11,12-carbonate 9-oxime (28) was obtained as a colourless foam, 0.68g. FAB m.s. 1185 MNa$^+$. Reductive methylation as in Example 4 gave erythromycin A 11,12-carbonate 9-oxime (4) identical with the product of Example 4.

EXAMPLE 13

Erythromycin A 11,12-carbonate 9-ethoxime (30)

To N,2'-O,4"-O-tribenzyloxycarbonyl-N-desmethylerythromycin A 11,12-carbonate 9-oxime (28) (see Example 12) (0.23g) in dry tetrahydrofuran (5ml) was added a 1M solution of tetrabutylammonium hydroxide in methanol (0.2ml). After 5 minutes at room temperature ethyl iodide (0.1ml) was added. After 30 minutes at room temperature the reaction mixture was diluted with diethyl ether (50ml) and brine (50ml). The solution was dried (magnesium sulphate) and evaporated under reduced pressure. The residue was purified by chromatography on silica gel eluting with 25% ethyl acetate in hexane to give the intermediate N,2'-O,4"-O-tribenzyloxy-carbonyl-N-desmethylerythromycin A 11,12-carbonate 9-ethoxime (29) (0.143g). FAB m.s. 1213 (MNa+). Use of the deprotection conditions given in Example 4 gave an 86% yield of the title compound (30), $[\alpha]^{20}D$ (1% in CHCl$_3$) −20.6°, $\nu_{max}$(CHCl$_3$) 1795, 1735 cm$^{-1}$ FAB m.s. 825 (MNa+).

EXAMPLE 14

Erythromycin A 11,12-carbonate 9-isopropyloxime (32)

This compound was prepared using the method of Example 13. The reaction was carried out using 0.269g of compound (28) and using isopropyl iodide (0.05ml) in place of the ethyl iodide. After a reaction time of 2.5h at room temperature, aqueous work-up and column chromatography on silica gel using 15-50% ethyl acetate in hexane as eluent gave N,2'-O-4"-O-tribenzyloxy-carbonyl-N-desmethylerythromycin A 11,12-carbonate 9-isopropyl-oxime (31), (0.133g). FAB m.s. 1227 (MNa+), 0.02g of recovered starting material (28) were also obtained. After deprotection of (31) using the procedure of Example 4, the title compound (32) was obtained in 68% yield as a colourless foam, $[\alpha]20D = -17.8°$ (1% in CHCl$_3$). $\nu_{max}$ (CHCl$_3$) 1795, 1735 cm$^{-1}$. FAB m.s. 841 (MNa+).

EXAMPLE 15

Erythromycin A 11,12-carbonate 9-carbamoylmethyloxime (34)

This compound was prepared using the method of Example 13. The reaction was carried out using 0.40g of compound (28) and using α-iodoacetamide (0.105g) in place of the ethyl iodide. After a reaction time of 30 minutes at room temperature, aqueous work-up and column chromatography on silica gel using 30% ethyl acetate in dichloro-methane as eluent gave N,2'-O,4"-O-tribenzyloxycarbonyl-N-desmethylerythromycin A 11,12-carbonate 9-carbamoylmethyloxime (33), 0.29g. $\nu_{max}$ 1800, 1735, 3 1685 cm$^{-1}$ After deprotection of (33) using the procedure of Example 4, the title compound (34) was obtained in 86% yield $[\alpha]^{20}D = -19.1°$ (1% in CHCl$_3$), $\nu_{max}$ (CHCl$_3$) 1795, 1735, 1680 cm$^{-1}$. FAB m.s. 854 (MNa+).

EXAMPLE 16

Erythromycin A 11,12-carbonate 9-methoxymethyloxime (36)

This compound was prepared using the method of Example 13. The reaction was carried out using 0.35g of compound (28) and using methoxymethyl chloride (0.05 ml) in place of the ethyl iodide. After a reaction time of 30 minutes at 0° C., aqueous work-up and column chromatography on silica gel using 10-30% ethyl acetate in dichloromethane as eluent gave N,2'-O,4"-O-tribenzyloxycarbonyl-N-desmethylerythromycin A 11,12-carbonate 9-methoxymethyloxime (35) (160mg). FAB m.s. 1229 (MNa+). Starting oxime (28) (0.11g) was also recovered. After deprotection of (35) using the method of Example 4, the title compound (36) was obtained in 79% yield. $[\alpha]^{20}D = -27.0$ (1% in CHCl$_3$), $\nu_{max}$ 1795, 1735, cm$^{-1}$ FAB m.s. 841 (MNa−).

EXAMPLE 17

Erythromycin A 11,12-carbonate 9-(2-methoxyethoxymethyl)oxime (38)

This compound was prepared using the method of Example 13. The reaction was carried out using 0.23g of compound (28) and using 2-methoxyethoxymethyl chloride (0.03 ml) in place of ethyl iodide. After a reaction time of 30 minutes at 0° C., aqueous work-up and column chromatography on silica gel using 15% ethyl acetate in dichloromethane gave N,2'-O,4"-O-tribenzyloxycarbonyl-N-desmethylerythromycin A 11,12-carbonate 9-methoxyethoxymethyl oxime (37), (0.15g). FAB m.s. 1273 (MNa+). After deprotection of (37) using the method of Example 4, the title compound (38) was obtained in 82% yield. $[\alpha]^{20}D = -34.1°$ (1% in CHCl$_3$). $\nu_{max}$ 1795, 1735 cm$^{-1}$ FAB m.s. 885 (MNa−).

EXAMPLE 18

Erythromycin A 11,12-carbonate 9-(2-hydroxyethyl)oxime (40)

N,2-O,4"-O-Tribenzyloxycarbonyl-N-desmethylerythromycin A 11,12-carbonate 9-oxime (28) (see Example 12) (0.24g) was taken up in dry dimethylformamide (2ml) and treated with 50% sodium hydride dispersion in oil (10mg). After stirring for 10 minutes at room temperature 2-benzyloxycarbonyloxyethyl iodide (0.077g) (prepared by treatment of bromoethanol with benzylchloroformate in the presence of pyridine, followed by treatment with sodium iodide in acetone) was added. After 20 minutes the reaction mixture was diluted with diethyl ether and washed with water and brine. The organic layer was dried (magnesium sulphate) and evaporated. The residue was purified by chromatography on silica gel using 10-15% ethyl acetate in dichloromethane to give N,2'-O,4"-O-tribenzyloxycarbonyl-N-desmethylerythromycin A 11,12-carbonate 9-(2-benzyloxycarbonyloxyethyl)oxime (39) (0.125g). This material was deprotected using the conditions of Example 4 to given the title compound (40) in 81% yield. $[\alpha]^{20}D = -26.3°$ (1.02% in CHCl$_3$). $\nu_{max}$ (CHCl$_3$) 3355(br), 1795, 1735 cm$^{-1}$ FAB m.s. 841 (MNa+).

EXAMPLE 19

Erythromycin 11,12-carbonate 9-methoxime (8)

Erythromycin A 9-methoxime (600 mg) in dry tetrahydrofuran (6 ml) was treated with powdered potassium carbonate (600 mg) and carbonyl diimidazole (500 mg). The mixture was stirred for 1.5 h. The mixture was diluted with ethyl acetate (50 ml) and was washed with water (3 × 30 ml). The solution was dried (Na$_2$SO$_4$) and the solvent was removed by evaporation under reduced pressure to give erythromycin 9-methoxime 4"-imidazolide as a white foam. The foam was dissolved in dry tetrahydrofuran (5 ml) and the solution was treated with carbonyl diimidazole (500 mg) and 50% sodium hydride dispersion in oil (80 mg). The mixture was stirred at 60° C. for 20 min. It was then cooled to room temperature and ethylene glycol (1 ml) was added. The mixture was stirred for 30 min. It was then diluted with ethyl acetate (50 ml) and was washed with water (3 × 30 ml). The solution was dried (Na$_2$SO$_4$)

and the solvent was removed under reduced pressure to give a white foam. The foam was chromatographed on silica gel using 1:9:90 0.880 NH$_3$/MeOH/CH$_2$Cl$_2$ to give the title compound (8) as a white solid (570 mg). Crystallisation from CH$_2$Cl$_2$/hexane gave colourless prisms, m.p. 230-231° C. Found C, 59.6; H, 8.8; N, 3.5; C$_{39}$H$_{68}$N$_2$O$_{14}$ requires C, 59.4; H, 8.7; N, 3.55%. Other properties were as described for the product from Example 5b.

EXAMPLE 20

2'-O,3'-N-Di(benzyloxycarbonyl)-des-N-methylerythromycin A 9-methoxime 11,12-carbonate (41)

2'-O,3'-N-Di(benzyloxycarbonyl)-des-N-methylerythromycin A 9-methoxime (6) (1.5g) in dry tetrahydrofuran (25ml) was treated with 50% sodium hydride dispersion in oil (150mg) and the mixture was stirred for 5 minutes. Carbonyl diimidazole (0.9g) was added and the mixture was stirred at 60° C. for 30 minutes. The mixture was cooled to room temperature and ethylene glycol (0.5ml) was added. After 10 minutes, the reaction was worked-up and chromatographed (as Example 5a) to give the title compound (41) as a white foam (1.52g), m.p. 115-118° C., [α]$^{22}$D −45.7° (c 1.0, CHCl$_3$) Found: C, 62.35; H, 7.65; N, 2.65. C$_{54}$H$_{78}$N$_2$O$_{18}$ requires C, 62.15; H, 7.55; N, 2.7%.

EXAMPLE 21

Erythromycin A 11,12-carbonate-9-(2-keto-1pyrrolidinylmethyl)oxime (43)

This compound was prepared using the method of Example 18. The reaction was carried out on a 0.96g scale using N-chloromethyl-2-ketopyrrolidine (0.12g) in place of benzyloxycarbonyloxyethyliodide. After a reaction time of 90 minutes at room temperature, aqueous work up, drying, evaporation, and chromatography using 1:1 ethyl acetate/hexane as eluent gave N,2'-O,4''-O-tribenzyl-oxycarbonyl-N-desmethylerythromycin A 11,12carbonate 9-(2-keto-1-pyrrolidinylmethyl)oxime (42) (0.48g, 46%).

This material was deprotected using the conditions of Example 4 to give the title compound (43) in 49% yield. [α]$^{20}$D −5.0° (1% in CHCl$_3$); ν$_{max}$(CHCl$_3$) 1795, 1735, 1685cm$^{-1}$. FAB m.s. 894 (MNa+).

EXAMPLE 22

Erythromycin A 11,12-carbonate-9-prop-2-enyloxime (45)

Erythromycin A oxime (1.5g, 2.01 mmol) was dissolved in dry tetrahydrofuran (20ml) and 1M tetrabutylammonium hydroxide in methanol (2.2ml) added. After five minutes at 20° C. prop-2-enyl bromide (0.19ml) was added. After a further fifteen minutes at 20° C. water and diethyl ether were added, the organic layer taken, dried (magnesium sulphate) and evaporated. The residue was crystallised from acetone/water to yield erythromycin A-prop-2-enyloxime (44) (1g, 63%) m.p. 106-107° C. [α]$^{20}$D = −65.7° (1% in CHCl$_3$). To the above oxime (0.4g, 0.51mmol) in dichloromethane (10ml) at 0° C. was added pyridine (0.5ml, 12 equivalents) and 12.5% w/w phosgene in toluene (2.2ml, 5 equivalents). After 90 minutes reaction time at 0° C. water (5ml) was added, the mixture stirred for ten minutes at room temperature before further dichloromethane was added. The organic phase was washed with brine, dried (magnesium sulphate), evaporated under reduced pressure, and the residue purified by chromatography on silica gel eluting with 0.880 ammonia/methanol/diethylether (1/10/200), to give the title compound (45), 0 38g, 91%. [α]$^{20}$D = −17.9° (1% in CHCl$_3$); ν$_{max}$ (CHCl$_3$) 1795, 1735cm$^{-1}$. FAB M.S. 837 (MNa+).

EXAMPLE 23

Erythromycin A 11,12-carbonate-9-n-propyloxime (46)

The propenyloxime carbonate (45), (0.2g, 0.25mmol) was hydrogenated in ethanol (15ml) over 10% palladium on carbon (50mg) at 20° C. and atmospheric pressure for 3 hours. After removal of the catalyst by filtration and evaporation of the solvent under reduced pressure the residue was purified by chromatography on silica gel eluting with 0.880 ammonia/methanol/dichloromethane (1:9:90) to give the title compound (46) (0.16g, 80%). [α]$^{20}$D −18.9° (1% in CHCl$_3$); ν$_{max}$ (CHCl$_3$) 1795, 1740cm$^{-1}$ FAB m.s. 839 (MNa+).

EXAMPLE 24

Erythromycin A 11,12-carbonate-9-ethoxymethyloxime (48)

Using the method of Example 22, erythromycin A oxime (1g) and ethoxymethyl chloride (0.134ml) gave erythromycin A ethoxymethyloxime (47), (0.55g, 51%) after chromatographic purification using 0.880 ammonia/methanol/dichloromethane (1:9:90) as eluent, the reaction being carried out at 0° C. for thirty minutes. After treatment of (47), (0.5g) with phosgene and pyridine, the title compound (48) was obtained in 77% yield. [α]$^{20}$D −38.5° (1% in CHCl$_3$); ν$_{max}$ (CHCl$_3$) 1795, 1735cm$^{-1}$ FAB m.s. 855 (MNa+).

EXAMPLE 25

Erythromycin A 11,12-carbonate-9-(2-dimethylaminoethyl)oxime (50)

Erythromycin A 9-(2-dimethylaminoethyl)oxime (49) was prepared by the method of Roussel (EP 33255, Example 5). The corresponding 11,12-carbonate was prepared from (49) on a 0.544g scale as in Example 22 to give the title compound (50), (0.35g, 63%). [α]$^{20}$D −39.6° (c = 1, CHCl$_3$); ν$_{max}$ (CHCl$_3$) 1795, 1735cm$^{-1}$. FAB m.s. 868 (MNa+).

EXAMPLE 26

Erythromycin A 11,12-carbonate-9-methylthio-methoxime (52)

The methylthiomethoxime (51) was prepared using the method of Example 22. The reaction was carried out on a 1g scale using methylthiomethyl chloride (0.13ml) as alkylating agent for 21 hours at room temperature. After normal aqueous work up chromatography (0.880 ammonia/methanol/dichloromethane 8/80/1000) gave erythromycin A 9-methylthiomethoxime(51), (0.378g, 35%) as a foam. Treatment of (51) (0.317g) with phosgene and pyridine gave the title compound (52), (0.27g, 70%) [α]$^{20}$D −50.2° (1% in CHCl$_3$); ν$_{max}$(CHCl$_3$) 1795, 1735cm$^{-1}$. FAB m.s. 857 (MNa+).

EXAMPLE 27

Erythromycin A 11,12-carbonate-9-cyclopentyloxime (54)

This compound was prepared using the method of Example 22. The reaction was carried out on a 1g scale (with respect to erythromycin A oxime) using cyclopentyl iodide (0.294g) as alkylating agent and with a reaction time of 22 hours at 20° C. After normal aqueous work up and chromatography (0.880 ammonia/methanol/dichloromethane 8:80:1000) erythromycin A 9-cyclopentyloxime (53), (0.367g, 34%) was obtained as a foam. Compound (53) (0.36g) was then converted to the title compound (54), (0.34g, 92%). $[\alpha]^{20}D$ −13.9° (1% in $CHCl_3$); $\nu_{max}$ ($CHCl_3$) 1795, 1735cm$^{-1}$ FAB m.s. 865 (MNa+).

EXAMPLE 28

Erythromycin A 11,12-carbonate-9-(2-methylprop-2-enyl)oxime (56)

Erythromycin A 2-methylprop-2-enyl oxime was prepared using the method of Example 22. The reaction was carried out on a 1g scale (with respect to erythromycin A oxime), using 1-chloro-2-methylprop-2-ene as alkylating agent and with a reaction time of 23h at room temperature. After aqueous work up and chromatography (0.880 ammonia/methanol/dichloromethane 8.80:1000) erythromycin A 9-(2-methyl-2-prop-2-enyl)oxime (55) (0.46g, 43%) was obtained as a foam. Compound (55) (0.46g) was then converted (as in Example 22) to the title compound (56), (0.38g, 80%) $[\alpha]^{20}D$ −16.3° (1% in $CHCl_3$); $\nu_{max}$ ($CHCl_3$) 1795, 1735cm$^{-1}$. FAB m.s. 851 (MNa+).

EXAMPLE 29

Erythromycin A 11,12-carbonate-9-(2-methylpropyl)oxime (57)

The methylpropenyloxime carbonate (56), (0.23g, 0.278mmol) was hydrogenated at 20° C. and atmospheric pressure in ethanol (15ml) over 10% palladium on carbon (70mg) for 100 minutes. After removal of the catalyst by filtration and evaporation of the solvent under reduced pressure the residue was purified by chromatography (0.880 ammonia/methanol/dichloromethane 6:60:1000) to give the title compound (57). (0.17g, 73%) $[\alpha]^{20}D$ −13.8° (1% in $CHCl_3$); $\nu_{max}$ ($CHCl_3$) 1795, 1735cm$^{-1}$. FAB m.s. 853 (MNa+).

EXAMPLE 30

Erythromycin A 11,12-carbonate-9-(2-oxopropyl)oxime (58)

The methylpropenyloxime carbonate (56) (0.2g) was dissolved in methanol (6ml), the solution cooled to −65° C., and glacial acetic acid (0.5ml) was added. Ozonised oxygen (2 equivalents of ozone) was bubbled in, the mixture left at −65° C. for twenty minutes, dimethyl sulphide (0.2ml) was added, and the mixture allowed to warm to room temperature. After evaporation of the solvent under reduced pressure, chromatography on silica gel eluting with 0.880 ammonia/methanol/dichloromethane (1:9:90) gave the title compound (58) (0.052g, 25%). $[\alpha]^{20}D$ −27.1° (1% in $CHCl_3$); $\nu_{max}$ ($CHCl_3$) 1795, 1735, 1730cm$^{-1}$. FAB m.s. 853 (MNa+).

EXAMPLE 31

Erythromycin A 11,12-carbonate-9-dimethylcarbamoylmethoxime (60)

Using the method of Example 13 with N,N-dimethyliodoacetamide (0.172g) as alkylating agent, N,2′-O,4′-O-tribenzyloxycarbonyl-N-desmethyl erythromycin A 11,12-carbonate-9-dimethylcarbamoylmethoxime (59) was obtained in 53% yield on a 0.811g scale; $\nu_{max}$ 1795, 1740, 1680, 1655cm$^{-1}$ FAB m.s. 1270 (MNa+). After deprotection of (59) using the procedure of Example 4, the title compound (60) was obtained in 76% yield on a 0.46g scale. $[\alpha]36.4°$ (1% in $CHCl_3$); $\nu_{max}$ ($CHCl_3$) 1795, 1740, 1660cm$^{-1}$. FAB m.s. 882 (MNa+).

EXAMPLE 32

Erythromycin A 11,12-carbonate-9-(2-methoxyethyl)oxime (62)

Erythromycin oxime (1g, 1.34mmol) was dissolved in dimethylformamide (8ml) and a 50% dispersion of sodium hydride in oil (0.072g, 1.5mmol) added. After stirring at 20° C. for ten minutes, 2-methoxyethyl bromide (0.21g) was added. After stirring at 20° .C for 2½ hours, water and diethylether were added, the organic layer washed with water and brine, dried (magnesium sulphate) evaporated under reduced pressure and purified by chromatography on silica gel eluting with 0.880 ammonia/methanol/diethylether (1:9:200) to yield erythromycin A 9-(2-methoxyethyl)oxime (61), (0.43g, 40%). The 11,12-carbonate was prepared on a 0.42g scale as in Example 22 to give the title compound (62), (0.23g, 53%) $[\alpha]^{20}D$ −34.3° (1% in $CHCl_3$); $\nu_{max}$ ($CHCl_3$) 1800, 1740cm$^{-1}$ FAB m.s. 855 (MNa+).

EXAMPLE 33

Erythromycin A 11,12-carbonate-9-methoxycarbonylmethyloxime (64)

This compound was prepared using the method of Example 32 The alkylation of erythromycin oxime was carried out on a 1g scale using methyl bromoacetate in place of methoxyethyl bromide to give, after purification by chromatography on silica gel eluting with 0.880 ammonia/methanol/dichloromethane (0.8:8:91), erythromycin A 9-methoxycarbonylmethyloxime (63), (0.38g, 35%). The 11,12-carbonate (64) was prepared on a 0.36g scale to give the title compound (64). (0.31g, 83%). $[\alpha]^{20}D$ −35.0 (1% in $CHCl_3$); $\nu_{max}$ ($CHCl_3$) 1795, 1740cm$^{-1}$. FAB m.s. 869 (MNa+).

EXAMPLE 34

Erythromycin A 11,12-carbonate-9-(2-pyridyl)methyloxime (66)

To erythromycin A oxime (1g, 1.34mmol) in dimethylformamide (8ml) was added 50% dispersion of sodium hydride in oil (0.124g, 3mmol) and 2-picolyl chloride hydrochloride (0.246g, 1.5mmol). The mixture was stirred at room temperature for 15 minutes. Water and ethyl acetate were added, the organic layer dried (magnesium sulphate) concentrated, and purified by crystallisation from acetone/water to give erythromycin A 9-(2-pyridyl)methyloxime (65), (0.67g, 50%) m.p. 105–108° C. The 11,12-carbonate was formed on a 0.44g scale as in Example 22, to yield the title compound (66). (0.31g, 68%). $[\alpha]^{20}D$ −30.6° (1% in $CHCl_3$); $\nu_{max}$ ($CHCl_3$) 1795, 1740cm$^{-1}$. FAB m.s. 888 (MNa+).

EXAMPLE 35

Erythromycin A 11,12-carbonate 9-isopropyloxime (32)

Erythromycin A oxime (1.0g, 1.34mmol) was dissolved in dimethylformamide (5 ml) and a 50% dispersion of sodium hydride in oil (0.064g, 1.33mmol) added. After stirring at 20° C. for 5 minutes isopropyl iodide (0.14ml) was added and the mixture stirred at 20° C. for a further 90 minutes. Water (20ml) was added and the precipitated solid collected by filtration, washed with water and dried. Recrystallisation from acetone/water gave erythromycin A 9-isopropyl oxime (67), (0.63g, 60%) m.p. 103–104° C. Formation of the 11,12-carbonate as in Example 22 gave the title compound (32). 56%, identical with the product of Example 14.

EXAMPLE 36

Erythromycin A 11,12-carbonate 9-isopropyloxime succinate salt (68)

To a suspension of the isopropyloxime carbonate (32), (0.099g, 0.12mmol) in water (5ml) was added a solution of succinic acid (0.0071g, 0.06mmol) in water (5ml). After sonication, a clear solution was obtained. This was filtered, and evaporated under reduced pressure to give the title compound (68) as a foam (0.10g, 95%).

EXAMPLE 37

Erythromycin A 11,12-carbonate-9-methoxymethyloxime hydrochloride salt (69)

To a suspension of the methoxymethyloxime carbonate (36), (0.10g, 0.12mmol) in water (1ml) was added aqueous hydrochloric acid (2.7ml, 0.05M). The clear solution was filtered and evaporated under reduced pressure to give the title compound (69) as a foam (0.10g, 97%).

EXAMPLE 38

6-O-Methylerythromycin A 11,12-carbonate 9-O-(methoxymethyl)oxime hydrogen succinate (70)

A solution of 6-0-methylerythromycin A 11,12-carbonate 9-0-(methoxymethyl)oxime (27) (0.117g) in ethanol (1ml) was treated with succinic acid (0.017g) in water (1.7ml). The clear solution was evaporated to dryness under reduced pressure to give the hydrogen succinate salt (70) in quantitative yield as a glassy solid.

We claim:

1. A compound of the formula I,

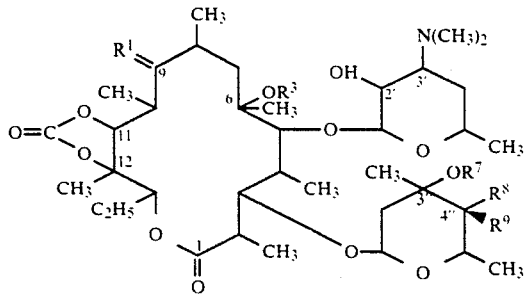

a pharmaceutically acceptable ester thereof or a pharmaceutically acceptable acid addition salt thereof wherein $R^1$ is unsubstituted or substituted oxime of the formula II

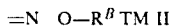

wherein
$R^B$ is hydrogen, unsubstituted or substituted alkyl of 1 to 6 carbon atoms, unsubstituted or substituted alkenyl of 2 to 6 carbon atoms, unsubstituted or substituted alkynyl of 2 to 6 carbon atoms, unsubstituted or substituted cycloalkyl of 3 to 7 carbon atoms, unsubstituted or substituted aryl, unsubstituted or substituted cycloalkyl alkyl of 3 to 7 carbon atoms in the cycloalkyl moiety and 1 to 6 carbon atoms in the alkyl moiety, unsubstituted or substituted arylalkyl of 1 to 6 carbon atoms in the alkyl moiety, unsubstituted or substituted alkylcycloalkyl of 1 to 6 carbon atoms in the alkyl moiety and 3 to 7 carbon atoms in the cycloalkyl moiety or unsubstituted or substituted alkylaryl of 1 to 6 carbon atoms in the alkyl moiety wherein the aryl moiety is phenyl or naphthyl and wherein the substituents are selected from the group consisting of heterocyclyl, amino, mono-, di- or tri- alkyl amino of 1 to 6 carbon atoms in the alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy, or $R^B$ is acyl; or $R^1$ is imino;

$R^3$ is hydrogen or alkyl of 1 to 6 carbon atoms unsubstituted or substituted by heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy; $R^7$ is hydrogen or methyl; one of $R^8$ and $R^9$ is hydrogen, hydroxy, alkoxy of 1 to 6 carbon atoms, alkanoyloxy of 1 to 6 carbon atoms, amino or $R^4$—$SO_2$—O—wherein $R^4$ is unsubstituted or substituted alkyl of 1 to 6 carbon atoms, unsubstituted or substituted alkenyl of 2 to 6 carbon atoms, unsubstituted or substituted aryl wherein aryl is as above defined, unsubstituted or substituted aralkyl wherein aryl is as above defined and the alkyl moiety is of 1 to 6 carbon atoms, unsubstituted or substituted aryloxyalkyl of 1 to 6 carbon atoms in the alkyl moiety wherein aryl is as above defined and wherein the substituent is selected from the group consisting of heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy; or $R^A$ it $R^G$—CH$_2$—CH$_2$—SO$_2$—O— wherein $R^G$ is amino, carbamoyl, sulphamoyl, ureido, thioureido, alkoxy of 1 to 6 carbon atoms, alkylthio of 1 to 6 carbon atoms, aryloxy wherein the aryl moiety is as above defined, arylthio wherein the aryl moiety is as above defined, or benzyloxy, and the other of $R^8$ and $R^9$ is hydrogen, or $R^8$ and $R^9$ together are oxo, oxime, or substituted oxime of the formula II

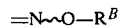     II wherein $R^B$ is as above defined.

2. A compound according to claim 1 which is selected from the group consisting of erythromycin A 11,12-carbonate 9-oxime; erythromycin A 11,12-carbonate 9-methoxime; 6-O-methylerythromycin A 11,12-carbonate 9-methoxime; 6-O-methylerythromycin A 11,12-carbonate 9-ethoxime; 6-O-methylerythromycin A 11,12-carbonate 9-oxime; 6-O-methylerythromycin A 11,12-carbonate 9-(2-methoxyethoxymethyl)oxime; 6-O-methylerythromycin A 11,12-carbonate 9-methoxymethyloxime; erythromycin A 11,12-carbonate 9-ethoxime; erythromycin A 11,12-carbonate 9-isopropyloxime; erythromycin A 11,12-carbonate 9-carbamoylmethyloxime; erythromycin A 11,12-carbonate 9-methoxymethyloxime; erythromycin A 11,12-carbonate 9-(2-methoxyethoxymethyl)oxime; erythromycin A 11,12-carbonate 9-(2-hydroxyethyl)oxime; erythromycin A 11,12-carbonate 9-(2-keto-1-pyrrolodinylmethyl)oxime; erythromycin A 11,12-carbonate-9-prop-2-enyloxime; erythromycin A 11,12-carbonate-9-n-propyloxime; erythromycin A 11,12-carbonate-9-ethoxymethyloxime; erythromycin A 11,12-carbonate-9-(2-dimethylaminoethyl)oxime; erythromycin A 11,12-carbonate-9-methylthiomethoxime; erythromycin A 11,12-carbonate-9-cyclopentyloxime; erythromycin A 11,12-carbonate-9-(2-methylprop-2-enyl)-oxime; erythromycin A 11,12-carbonate-9-(2-methylpropyl)oxime; erythromycin A 11,12-carbonate-9-(2-oxopropyl)oxime; erythromycin A 11,12-carbonate-9-dimethyl-carbamoylmethoxime; erythromycin A 11,12-carbonate-9-(2-methoxyethyl)oxime; erythromycin A 11,12-carbonate-9-methoxycarbonylmethyloxime; erythromycin A 11,12-carbonate-9-(2-pyridyl)methyloxime; erythromycin A 11,12-carbonate 9-isopropyloxime, a pharmaceutically acceptable ester thereof and a pharmaceutically acceptable acid addition salt thereof.

3. A pharmaceutical composition useful for treating bacterial infections in humans and animals which comprises an antibacterially effective amount of the compound of the formula I,

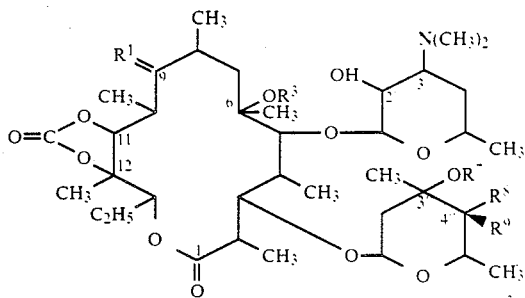

a pharmaceutically acceptable ester thereof or a pharmaceutically acceptable acid addition salt thereof wherein $R^1$ is unsubstituted or substituted oxime of the formula II

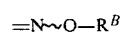     II wherein $R^B$ is hydrogen, unsubstituted or substituted alkyl of 1 to 6 carbon atoms, unsubstituted or substituted alkenyl of 2 to 6 carbon atoms, unsubstituted or substituted alkynyl of 2 to 6 carbon atoms, unsubstituted or substituted cycloalkyl of 3 to 7 carbon atoms, unsubstituted or substituted aryl, unsubstituted or substituted cycloalkyl alkyl of 3 to 7 carbon atoms in the cycloalkyl moiety and 1 to 6 carbon atoms in the alkyl moiety, unsubstituted or substituted arylalkyl of 1 to 6 carbon atoms in the alkyl moiety, unsubstituted or substituted alkylcycloalkyl of 1 to 6 carbon atoms in the alkyl moiety and 3 to 7 carbon atoms in the cycloalkyl moiety or unsubstituted or substituted alkylaryl of 1 to 6 carbon atoms in the alkyl moiety wherein the aryl moiety is phenyl or naphthyl and wherein the substituents are selected from the group consisting of heterocyclyl, amino, mono-, di- or tri- alkyl amino of 1 to 6 carbon atoms in each alkyl moiety, alkanoyl amino of 1 to 6 carbon atoms in the alkyl moiety hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy, or $R^B$ is acyl; or $R^1$ is imino;

$R^3$ is hydrogen or alkyl of 1 to 6 carbon atoms unsubstituted or substituted by heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy; $R^7$ is hydrogen or methyl; one of $R^8$ and $R^9$ is hydrogen, hydroxy, alkoxy of 1 to 6 carbon atoms, alkanoyloxy of 1 to 6 carbon atoms, amino or $R^d$—$SO_2$—O—wherein $R^d$ is unsubstituted or substituted alkyl of 1 to 6 carbon atoms, unsubstituted or substituted alkenyl of 2 to 6 carbon atoms, unsubstituted or substituted aryl wherein aryl is as above defined, unsubstituted or substituted aralkyl wherein aryl is as above defined and the alkyl moiety has 1 to 6 carbon atoms, unsubstituted or substituted aryloxyalkyl of 1 to 6 carbon atoms in the alkyl moiety wherein aryl is as above defined and wherein the substituent is selected from the group consisting of heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy; or $R^d$ is $R^G$—$CH_2$—$CH_2$—$SO_2$—O—wherein $R^G$ is amino, carbamoyl, sulphamoyl, ureido, thioureido, alkoxy of 1 to 6 carbon atoms, alkylthio of 1 to 6 carbon atoms, aryloxy wherein the aryl moiety is as above defined, arylthio wherein the aryl moiety is as above defined, or benzyloxy, and the other of $R^8$ and $R^9$ is hydrogen, or $R^8$ and $R^9$ together are oxo, oxime, or substituted oxime or the formula II

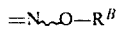 II wherein $R^B$ is as above defined, in combination with a pharmaceutically acceptable carrier.

4. A composition according to claim 3 wherein the compound is selected from the group consisting of erythromycin A 11,12-carbonate 9-oxime; erythromycin A 11,12-carbonate 9-methoxime; 6-O-methylerythromycin A 11,12-carbonate 9-methoxime; 6-O-methylerythromycin A 11,12-carbonate 9-ethoxime; 6O-methylerythromycin A 11,12-carbonate 9-oxime; 6-O-methylerythromycin A 11,12-carbonate 9-(2-methoxyethoxymethyl)oxime; 6-O-methylerythromycin A 11,12-carbonate 9-methoxymethyloxime; erythromycin A 11,12-carbonate 9-ethoxime; erythromycin A 11,12-carbonate 9-isopropyloxime; erythromycin A 11,12-carbonate 9-carbamoylmethyloxime; erythromycin A 11,12-carbonate 9-methoxymethyloxime; erythromycin A 11,12-carbonate 9-(2-methoxyethoxymethyl)oxime; erythromycin A 11,12-carbonate 9-(2-hydroxyethyl)oxime; erythromycin A 11,12-carbonate 9-(2-keto-1-pyrrolidinylmethyl)oxime; erythromycin A 11,12-carbonate-9-prop-2-enyloxime; erythromycin A 11,12-carbonate-9-n-propyloxime; erythromycin A 11,12-carbonate-9-ethoxymethyloxime; erythromycin A 11,12-carbonate-9-(2-dimethylaminoethyl)oxime; erythromycin A 11,12-carbonate-9-methylthiomethoxime; erythromycin A 11,12-carbonate-9-cyclopentyloxime; erythromycin A 11,12-carbonate-9-(2-methylprop-2-enyl)-oxime; erythromycin A 11,12-carbonate-9-(2-methylpropyl)oxime; erythromycin A 11,12-carbonate-9-(2-oxopropyl)oxime; erythromycin A 11,12-carbonate-9-dimethylcarbamoylmethoxime; erythromycin A 11,12-carbonate-9-(2-methoxyethyl)oxime; erythromycin A 11,12-carbonate-9-methoxycarbonylmethyloxime; erythromycin A 11,12-carbonate-9-(2-pyridyl)methyloxime; erythromycin A 11,12-carbonate 9-isopropyloxime, a pharmaceutically acceptable ester thereof and a pharmaceutically acceptable acid addition salt thereof.

5. A method of treating bacterial infections in humans and animals which comprises administering to a human or animal in need thereof an antibacterially effective amount of a compound of the formula I,

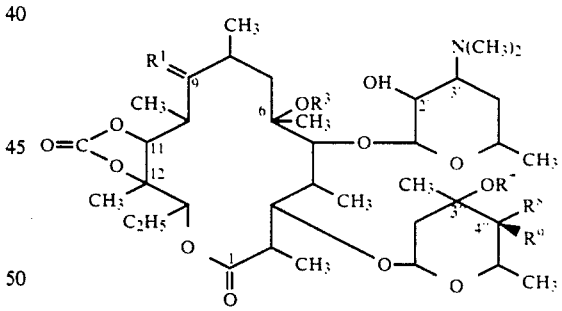

a pharmaceutically acceptable ester thereof or a pharmaceutically acceptable acid addition salt thereof wherein $R^1$ is unsubstituted or substituted oxime of the formula II

 TM II wherein $R^B$ is hydrogen, unsubstituted or substituted alkyl of 1 to 6 carbon atoms, unsubstituted or substituted alkenyl of 2 to 6 carbon atoms, unsubstituted or substituted alkynyl of 2 to 6 carbon atoms, unsubstituted or substituted cycloalkyl of 3 to 7 carbon atoms, unsubstituted or substituted aryl, unsubstituted or substituted cycloalkyl alkyl of 3 to 7 carbon atoms in the cycloalkyl moiety and 1 to 6 carbon atoms in the alkyl moiety, unsubstituted or substituted arylalkyl of 1 to 6 carbon atoms in the alkyl moiety, unsubstituted or substituted alkylcycloalkyl of 1 to 6 carbon atoms in the alkyl moiety and 3 to 7 carbon atoms in the cycloalkyl moiety or unsubstituted or substituted alkylaryl of 1 to 6 carbon atoms in the alkyl moiety wherein the aryl moiety is phenyl or naphthyl and wherein the substituents are selected from the group consisting of heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy, or $R^B$ is acyl; or $R^1$ is imino;

$R^3$ is hydrogen or alkyl of 1 to 6 carbon atoms unsubstituted or substituted by heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy wherein aryl is as above defined, aralkyloxy wherein the aryl moiety is as above defined and the alkyl moiety is of 1 to 6 carbon atoms, mercapto, alkylithio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above define, and heterocyclylcarbonyloxy; $R^7$ is hydrogen or methyl; one of $R^8$ and $R^9$ is hydrogen, hydroxy, alkoxy of 1 to 6 carbon atoms, alkanoyloxy of 1 to 6 carbon atoms, amino or $R^d$—$SO_2$—O—wherein $R^d$ is unsubstituted or substituted alkyl of 1 to 6 carbon atoms, unsubstituted or substituted alkenyl of 2 to 6 carbon atoms, unsubstituted or substituted aryl wherein aryl is as above defined, unsubstituted or substituted aralkyl wherein aryl is as above defined and the alkyl moiety is of 1 to 6 carbon atoms, unsubstituted or substituted aryloxyalkyl of 1 to 6 carbon atoms in the alkyl moiety wherein aryl is as above defined and wherein the substituent is selected from the group consisting of heterocyclyl, amino, mono-, di- or tri- alkyl amino of 1 to 6 carbon atoms in each alkyl moiety, alkanoyl amino of 1 to 6 carbon atoms in the alkyl moiety, hydroxy, alkoxy of 1 to 6 carbon atoms, alkoxyalkoxy of 1 to 6 carbon atoms in each alkoxy moiety, alkenyloxy of 2 to 6 carbon atoms, alkynyloxy of 2 to 6 carbon atoms, aryloxy as above defined, aralkyloxy wherein the aryl moiety is as above defined and the alkyl moiety is of 1 to 6 carbon atoms, mercapto, alkylthio of 1 to 6 carbon atoms, alkenylthio of 2 to 6 carbon atoms, alkynylthio of 2 to 6 carbon atoms, arylthio wherein aryl is as above defined, aralkylthio wherein the aryl moiety is above defined and the alkyl moiety is of 1 to 6 carbon atoms, heterocyclylthio, sulphamoyl, carbamoyl, amidino, guanidino, nitro, oxo, formyl, chloro, bromo, fluoro, cyano, thiocyanato, carboxy, a carboxyl salt, a carboxyl ester, alkanoyloxy of 1 to 6 carbon atoms, acyl, arylcarbonyloxy wherein aryl is as above defined, and heterocyclylcarbonyloxy; or $R^d$ is $R^G$—$CH_2$—$CH_2$—$SO_2$—O—wherein $R^G$ is amino, carbamoyl, sulphamoyl, ureido, thioureido, alkoxy of 1 to 6 carbon atoms, alkylthio of 1 to 6 carbon atoms, aryloxy wherein the aryl moiety is as above defined, arylthio wherein the aryl moiety is as above defined, or benzyloxy, and the other of $R^8$ and $R^9$ is hydrogen, or $R^8$ and $R^9$ together are oxo, oxime, or substituted oxime of the formula II

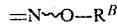   II wherein $R^B$ is as above defined, in combination with a pharmaceutically acceptable carrier.

6. A method according to claim 5 wherein the compound is selected from the group consisting of erythromycin A 11,12-carbonate 9-oxime; erythromycin A 11,12-carbonate 9-methoxime; 6O-methylerythromycin A 11,12-carbonate 9-methoxime; 6O-methylerythromycin A 11,12-carbonate 9-ethoxime; 6O-methylerythromycin A 11,12-carbonate 9-oxime; 6-O-methylerythromycin A 11,12-carbonate 9-(2-methoxyethoxymethyl)oxime; 6-O-methylerythromycin A 11,12-carbonate 9-methoxymethyloxime; erythromycin A 11,12-carbonate 9-ethoxime; erythromycin A 11,12-carbonate 9-isopropyloxime; erythromycin A 11,12-carbonate 9-carbamoylmethyloxime; erythromycin A 11,12-carbonate 9-methoxymethyloxime; erythromycin A 11,12-carbonate 9-(2-methoxyethoxymethyl)oxime; erythromycin A 11,12-carbonate 9-(2-hydroxyethyl)oxime; erythromycin A 11,12-carbonate 9-(2-keto-1-pyrrolidinylmethyl)oxime; erythromycin A 11,12-carbonate-9-prop-2-enyloxime; erythromycin A 11,12-carbonate-9-n-propyloxime; erythromycin A 11,12-carbonate-9-ethoxymethyloxime; erythromycin A 11,12-carbonate-9-(2-dimethylaminoethyl)oxime; erythromycin A 11,12-carbonate-9-methylthiomethoxime; erythromycin A 11,12-carbonate-9-cyclopentyloxime; erythromycin A 11,12-carbonate-9-(2-methylprop-2-enyl)-oxime; erythromycin A 11,12-carbonate-9-(2-methylpropyl)oxime; erythromycin A 11,12-carbonate-9-(2-oxopropyl)oxime; erythromycin A 11,12-carbonate-9-dimethylcarbamoylmethoxime; erythromycin A 11,12-carbonate-9-(2-methoxyethyl)oxime; erythromycin A 11,12-carbonate-9-methoxycarbonylmethyloxime; erythromycin A 11,12-carbonate-9-(2-pyridyl)methyloxime; erythromycin A 11,12-carbonate 9-isopropyloxime, a pharmaceutically acceptable ester thereof and a pharmaceutically acceptable acid addition salt thereof.

* * * * *